United States Patent
Butscher et al.

(10) Patent No.: US 6,732,558 B2
(45) Date of Patent: May 11, 2004

(54) ROBOT AND METHOD FOR BENDING ORTHODONTIC ARCHWIRES AND OTHER MEDICAL DEVICES

(75) Inventors: Werner Butscher, Berlin (DE); Friedrich Riemeier, Berlin (DE); Rüdger Rubbert, Berlin (DE); Thomas Weise, Berlin (DE); Rohit Sachdeva, Plano, TX (US)

(73) Assignee: OraMetrix, Inc., Richardson, TX (US)

( * ) Notice: Subject to any disclaimer, the term of this patent is extended or adjusted under 35 U.S.C. 154(b) by 0 days.

(21) Appl. No.: 10/260,763

(22) Filed: Sep. 27, 2002

(65) Prior Publication Data

US 2003/0070468 A1 Apr. 17, 2003

Related U.S. Application Data

(62) Division of application No. 09/834,967, filed on Apr. 13, 2001, now Pat. No. 6,612,143.

(51) Int. Cl.$^7$ .............................. B21D 11/10; A61C 3/00
(52) U.S. Cl. ...................... 72/21.4; 72/295; 72/342.7; 72/342.92
(58) Field of Search ................................ 72/21.4, 21.5, 72/342.7, 342.8, 342.92, 308, 307, 311, 310, 306, 295, 342.96; 433/2, 3

(56) References Cited

U.S. PATENT DOCUMENTS

| | | | | |
|---|---|---|---|---|
| 2,335,165 A | * | 11/1943 | Westin et al. ............... | 219/149 |
| 3,302,437 A | * | 2/1967 | Dolney ....................... | 72/296 |
| 4,043,364 A | | 8/1977 | Rose .......................... | 140/106 |
| 4,061,005 A | * | 12/1977 | Kawanami et al. .......... | 72/21.4 |
| 4,163,183 A | | 7/1979 | Engelberger et al. ........ | 318/567 |
| 4,184,259 A | | 1/1980 | Sosnay ....................... | 433/4 |
| 4,186,487 A | | 2/1980 | Wallshein .................... | 433/20 |
| 4,527,410 A | * | 7/1985 | MacNitt et al. .............. | 72/306 |
| 4,656,860 A | | 4/1987 | Orthuber et al. ............. | 72/299 |
| RE32,794 E | | 12/1988 | Engelberger et al. ........ | 414/730 |
| 4,829,219 A | | 5/1989 | Penkar ........................ | 318/568.18 |
| 4,878,369 A | * | 11/1989 | Apps et al. .................. | 72/18.7 |
| 4,945,747 A | | 8/1990 | Yogo .......................... | 72/306 |
| 4,964,800 A | | 10/1990 | Good .......................... | 433/3 |
| 4,983,120 A | | 1/1991 | Coleman et al. ............. | 433/24 |
| 5,011,406 A | | 4/1991 | Wildman ..................... | 433/24 |
| 5,084,935 A | | 2/1992 | Kalthoff ...................... | 7/132 |
| 5,100,316 A | | 3/1992 | Wildman ..................... | 433/24 |

(List continued on next page.)

*Primary Examiner*—Daniel C. Crane
(74) *Attorney, Agent, or Firm*—McDonnell Boehnen Hulbert & Berghoff

(57) ABSTRACT

A robotic bending apparatus for bending archwires and other types of elongate, bendable medical devices into a desired configuration includes a first gripping tool and a moveable gripping tool. The first gripping tool can be either fixed with respect to a base or table for the robot or positioned at the end of robot am. The moveable gripping tool is mounted to the end of a moveable robot arm having a proximal portion also mounted to the base. The robot preferably comprises a six axis bending robot, in which the distal end of the moveable arm can move relative to the fixed gripping tool about three translational axes and three rotational axes. The gripping tools preferably incorporate force sensors which are used to determine overbends needed to get the desired final shape of the archwire. The robot may also include a resistive heating system in which current flows through the wire while the wire is held in a bent condition to heat the wire and thereby retain the bent shape of the wire. A magazine for holding a plurality of straight archwires needing to be bent and a conveyor system for receiving the wires after the bending process is complete are also described. The robot bending system is able to form archwires with any required second and third order bends quickly and with high precision. As such, it is highly suitable for use in a precision appliance-manufacturing center manufacturing a large number of archwires (or other medical devices or appliances) for a distributed base of clinics.

3 Claims, 22 Drawing Sheets

U.S. PATENT DOCUMENTS

| | | |
|---|---|---|
| 5,291,771 A | 3/1994 | Tomo et al. .................. 72/306 |
| 5,295,886 A | 3/1994 | Wildman ..................... 433/24 |
| 5,359,872 A | 11/1994 | Nashiki ........................... 72/9 |
| 5,431,562 A | 7/1995 | Andreiko et al. ............. 433/24 |
| 5,447,432 A | 9/1995 | Andreiko et al. ............. 433/24 |
| 5,624,258 A | 4/1997 | Wool .......................... 433/20 |
| 5,683,243 A | 11/1997 | Andreiko et al. ............... 433/3 |
| 5,765,426 A | 6/1998 | Saegusa ...................... 72/306 |
| 5,836,188 A | 11/1998 | Mahan et al. ................ 72/21.4 |
| 5,875,665 A * | 3/1999 | Yamamoto et al. .......... 72/21.1 |
| 5,937,505 A * | 8/1999 | Strong et al. ................. 29/593 |
| 6,015,289 A | 1/2000 | Andreiko et al. ............... 433/3 |
| 6,035,775 A * | 3/2000 | Nghiem ....................... 100/43 |
| 6,185,968 B1 | 2/2001 | Kanamori ................... 72/14.8 |
| 6,214,285 B1 | 4/2001 | Rubbert et al. ................ 266/87 |
| 6,234,913 B1 * | 5/2001 | Bomcke ...................... 470/34 |
| 6,430,979 B1 * | 8/2002 | Meier ........................ 72/21.4 |

\* cited by examiner

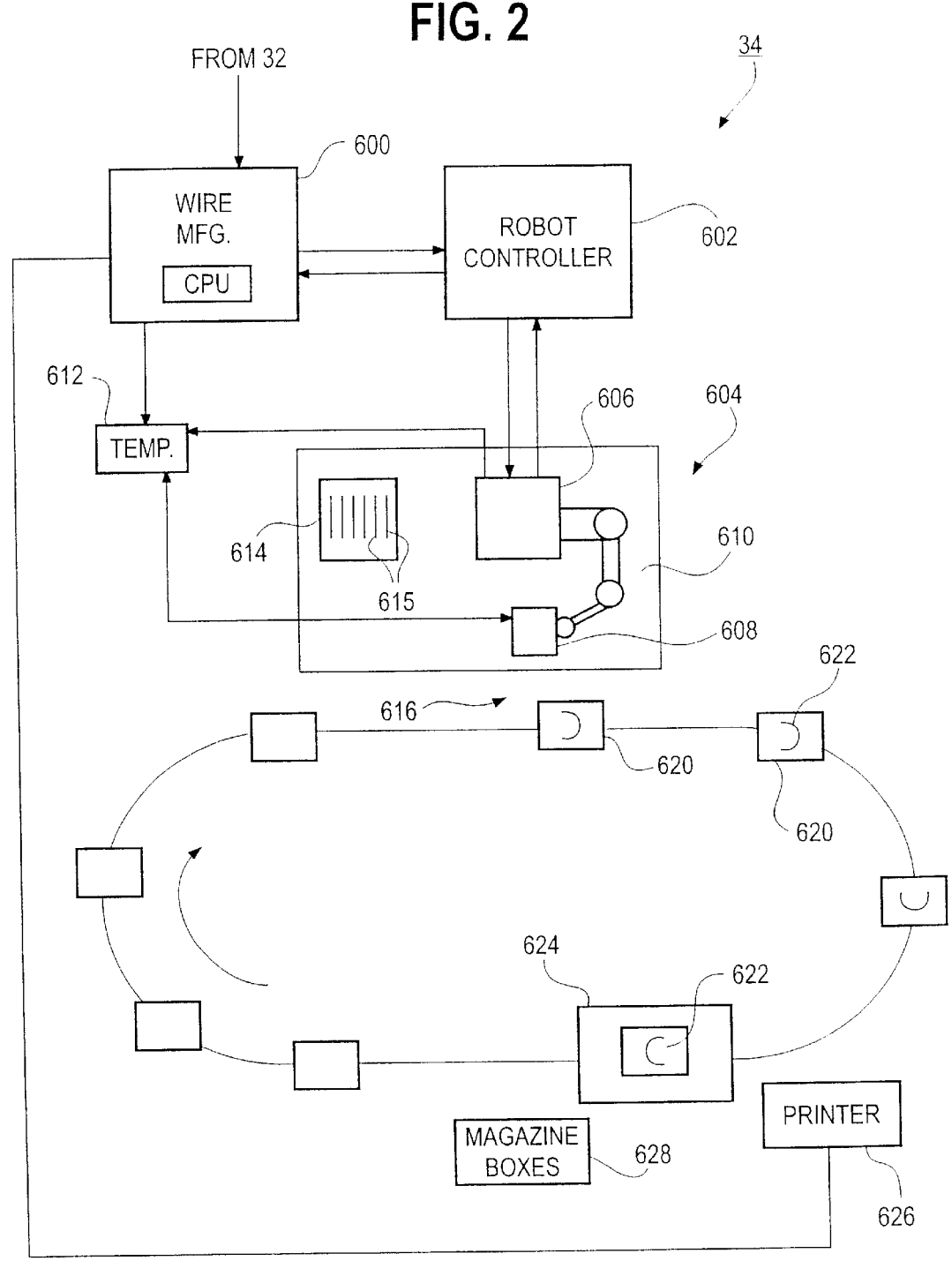

FIG. 18
$$\begin{bmatrix} 0.4 & -0.7 & 0 & -22 \\ 0.9 & 0.7 & 0 & 21 \\ 0 & 0.14 & 0 & 2 \\ 0 & 0 & 0 & 1 \end{bmatrix}$$
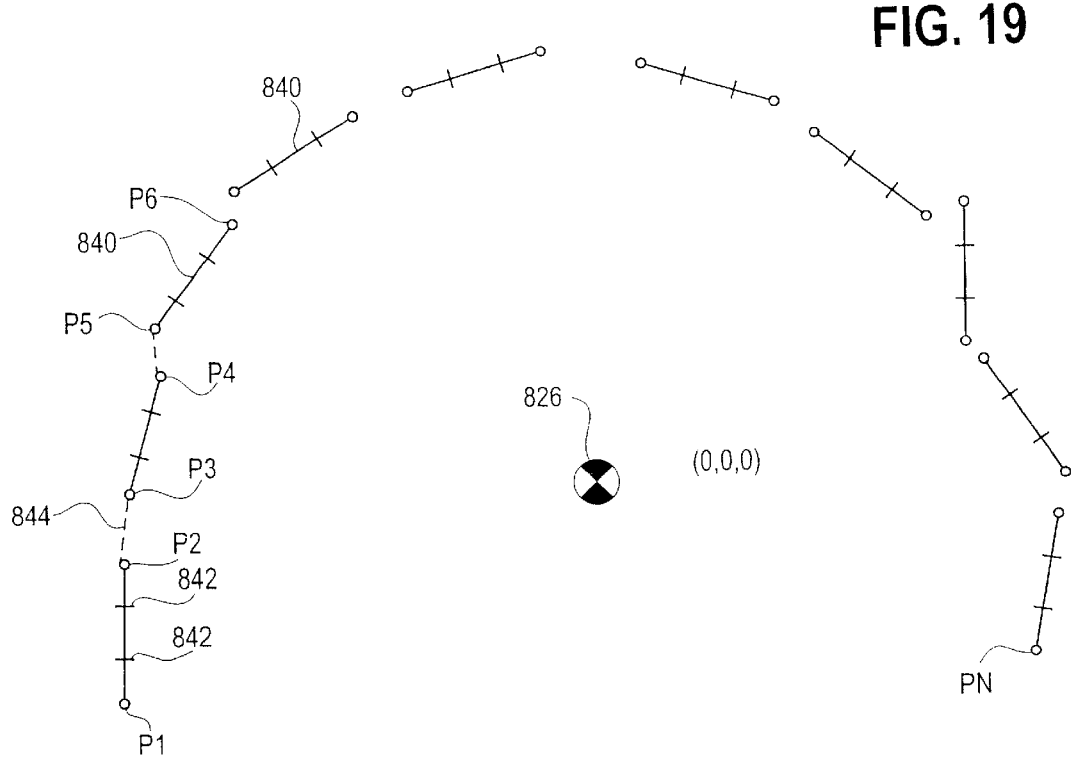
FIG. 19
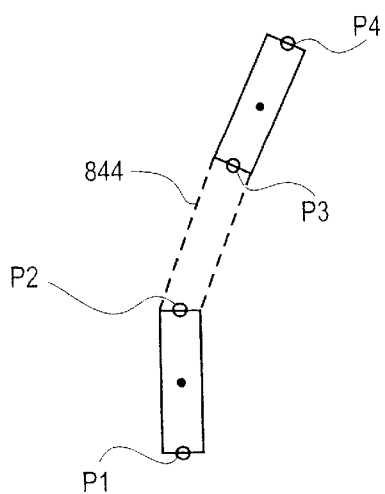
FIG. 20

1ST MOTION

2ND MOTION

ROBOT AND METHOD FOR BENDING ORTHODONTIC ARCHWIRES AND OTHER MEDICAL DEVICES

CROSS-REFERENCE TO RELATED APPLICATION

This application is a divisional application of Ser. No. 09/834,967 filed Apr. 13, 2001, now U.S. Pat. No. 6,612,143 the contents of which are incorporated by reference herein.

BACKGROUND OF THE INVENTION

A. Field of the Invention

This invention relates to a robot and method for automatically bending orthodontic archwires, retainers, or other orthodontic or medical devices into a particular shape.

B. Description of Related Art

In orthodontics, a patient suffering from a malocclusion is treated by affixing brackets to the surface of the teeth and installing an archwire in the slots of the brackets. The archwire and brackets are designed to generated a customized force system that applies forces to teeth, by which individual teeth are moved relative to surrounding anatomical structures into a desired occlusion. There are two approaches to designing an appropriate force system for a patient. One is based on a flat archwire and customized brackets, e.g., Andreiko et al., U.S. Pat. No. 5,447,432. The other is based on off-the shelf brackets and designing a customized archwire that has complex bends designed to move or rotate the teeth in the desired direction. Traditionally, the latter approach has required manual bending of the archwire by the orthodontist.

Machines for bending orthodontic archwires have been proposed in the prior art. Andreiko et al. describes an apparatus that takes a straight archwire and imparts a simple planar arcuate curvature to the wire. The wire is customized in the sense that the shape of the arc is designed for a particular patient, but the wire bending apparatus described in Andreiko et al. is limited to a customized bracket approach to orthodontics. In particular, the Andreiko et al. wire bending apparatus cannot produce any complex and twists bends in the wire, e.g., bends requiring a combination of translation and rotational motion.

The patent to Orthuber et al., U.S. Pat. No. 4,656,860 describes a bending robot for bending archwires. A robot as described in the '860 patent was developed by the predecessor of the assignee of the present invention and used experimentally for several years, but never widely commercialized. The robot consisted of two characteristic design features: a bending cone that could move forwards and backwards to bend the wire, and a rotating cone that could twist the wire. As such, it could only apply torque or bends over the two main axes of a cross section of a rectangular shaped wire. Since the portion of the wire extending beyond the cone is free and unconstrained, the robot had no control as to the effective deformation of the wire. Additionally, a series of three twists and two bends were typically required by a robot in accordance with the '860 patent to shape an archwire so that it would fit in the slots of two adjacent brackets. This series of twists and bends required as much as 5 mm of wire length between adjacent brackets. This length of wire is greater than that available for closely spaced teeth, such as the lower front teeth. To avoid this situation, the robot bent a twisted portion of the wire, which provoked uncontrolled rotational motion in the wire.

The design of the '860 patent also has other shortcomings: it provides no means for measuring forces imparted by the wire since one end of the wire is free and the wire is gripped immediately below the bending point. The robot had no effective feedback mechanism for detecting how the wire in fact was bent after a particular bending or twisting operation was performed. As the free end of the wire is not constrained or held in any manner, there is no ready way to heat the wire as it is being bent in order to fix the shape of the bend in a wire made from a shape memory material. Consequently, shape memory alloy wires made with the '860 patent were subject to a separate heating treatment in a separate thermal device.

The present invention presents a substantial improvement to the robot of the '860 patent. The invention also provides for much greater flexibility in the design and manufacture of archwires than that disclosed by the Andreiko et al. patent. In particular, the present invention enables the manufacture of custom, highly accurate orthodontic archwires. Such wires are ideally suited to an archwire-based orthodontic treatment regime based on standard, off-the-shelf brackets. The invention is also readily adaptable to bending other medical devices, including implants such bone fixation plates, prostheses, orthotic devices, and even surgical tools.

SUMMARY OF THE INVENTION

In a first aspect, a bending apparatus or machine is provided for bending an orthodontic appliance, such as a retainer or archwire, into a desired configuration. While the orthodontic device is described as being an archwire in the illustrated embodiment, other types of medical devices are contemplated as the type of article capable of being bent by the robot. Examples of such medical devices are prostheses, orthotic devices, implants, fixation plates, spectacle frames, and surgical devices such as a reamer for root canals.

The bending apparatus or machine may take the form of a robot mounted to a base or table support surface. A first gripper tool is provided. This tool can either be fixed with respect to the base or may be incorporated into a moveable arm. The first gripping tool has a first gripping structure for holding the archwire or other medical device. The bending apparatus includes a moveable arm having a proximal portion mounted to the base a distance away from the first gripper tool and a free distal end portion. The moveable arm is constructed such that the free distal portion of the moveable arm is capable of independent movement relative to the first gripper tool along at least one translation axis and about at least one rotation axis. In an illustrated embodiment, the moveable arm has a set of joints which allows the distal end of the arm to move in 6 degrees of freedom –3 orthogonal translational axes and 3 orthogonal rotational axes. However, depending on the nature of the medical device and the required bends to form in the device, a lesser number of degrees of freedom may be appropriate, reducing the cost and complexity of the bending apparatus.

A second gripping tool is mounted to the distal portion of the moveable arm. The second gripping tool has a gripping structure for gripping the archwire. Thus, the archwire is gripped by the first and second gripping tools, with the second, moveable gripping tool capable of motion relative to the first gripping tool along at least one translational axis and at least one rotational axis.

The robot further includes a control system operative of the moveable arm and the first and second gripping tools so as to cause the first and second gripping tools to grip the archwire while the gripping tools are separated from each other and to cause the second gripping tool to move about at least one of the rotational axis and translation axis to thereby bend the archwire a desired amount. Preferably, the control system reads an input file containing information as to the shape of the archwire (or location of bending points along the wire) and responsively operates the moveable arm and first and second gripping tools to form a series of bends and/or twists in the archwire.

The nature of the bends in the archwire will be dictated by the orthodontic prescription and the type of force system that the orthodontist has chosen for the patient. Complex bends involving a combination of bends and twists are possible with the robot. For such complex bends, it has been found that a six-axis robot, in which the second gripping tool is capable of movement relative to the first gripping tool about three translation axes and three rotation axes, is a preferred embodiment.

Orthodontic archwires and other medical devices may have elastic properties such that when a certain amount of force is applied to the workpiece, it returns to its original configuration at least to some degree. What this means is that when a certain bend is formed in the wire, say a 10 degree bend, the wire may take a shape of an 8 degree bend due to this elastic property. Hence, some overbending of the archwire may be needed to account for this elastic deformation. Solutions for overbending wire are provided. One method is a force-based approach. In this approach, the robot comprises a force sensor system for detecting forces generated by the wire after the wire has been bent by the first and second gripping tools. Depending on the direction and magnitude of the detected forces, additional bends are formed in the wire. The proper bend in the wire is deemed to exist when the wire, at its designed shape, exhibits zero or substantially zero forces.

An alternative approach to overbending is based on deformation. In this approach, the wire is bent, the wire is released from the moveable gripping tool and a measurement is made of the wire's shape, the wire is bent some more (assuming more bending is required), the wire is released again, and the process continues until the resulting configuration is the one specified by the input file. In this embodiment, a camera or other optical technique can be used to measure the shape of the wire. Alternatively, force sensors can be used to determine the actual bend in the wire (by moving the moveable gripper holding the wire to the position where no forces are measured), and a measurement is taken to indicate what additional bends, if any, are needed to result in the desired configuration.

It is further contemplated that a database of overbending information can be acquired as the robot bends wires. This database of overbending information can be used by artificial intelligence programs to derive a relationship between overbending and desired bends, for a particular archwire material. It may be possible to overbend wires in a single step, that is without requiring a lot of intermediate bending steps, based on this database of information, or based on a derived relationship between overbending and resulting wire shape.

In another aspect, the robot includes a heating system to apply heat to the archwire or other workpiece while it is in the bent condition and/or during bending. A current-based resistive heating system and heated grippers are used in the illustrated embodiment. This system allows shape memory alloys to be bent by the robot and the acquired bends retained in the wire material. Other heating systems are possible depending on the nature of the device being bent.

In another aspect, the robot is part of an archwire manufacturing system including a magazine containing a plurality of straight archwires. The magazine holds the archwires such that they are spaced from each other so as to enable the robot to grip an individual one of the archwires. Several different magazine designs are proposed. After the robot has formed the archwire, the archwire is placed at a finish location. A conveyor system carries the finished archwire from the finish location to a labeling and packaging station. The wires are individually labeled and packaged. Alternatively, pairs of wires could be labeled as corresponding to a single patient and packaged together.

In still another aspect, a gripping tool for a bending robot is provided. The gripping tool includes a pair of opposing gripping fingers moveable between open and closed positions, and a force system coupled to the gripping fingers for detecting forces imparted by a workpiece such as an archwire or other medical device after a bend has been placed in the workpiece. As noted above, the force system can be used to measure resulting forces after a certain bend has been placed in the wire, and the measurements used to indicate additional bending steps to yield the required configuration taking into account the need for overbending.

In still another aspect of the invention, a method is provided for bending an orthodontic archwire in a bending robot. The method includes the steps of a) gripping the archwire with a first gripping tool such that a portion of the archwire projects beyond the first gripping tool;

b) gripping the portion of the archwire extending beyond the first gripping tool with a moveable gripping tool;

c) releasing the gripping of the archwire by the first gripping tool;

d) moving the moveable gripping tool while gripping the archwire so as to draw the archwire through the first gripping tool a predetermined amount;

e) the first gripping tool again gripping said archwire after the step of moving is performed, and f) moving the moveable gripping tool relative to the first gripping tool so as to place a bend in the archwire having a desired configuration.

In the above method, the moveable gripping tool and first gripping tool can cooperate to place a series of bends in the archwire. It has been found that the movement called for by step f) should be performed such that a constant distance, equal to the length of archwire pulled through the fixed gripping tool in step d) is maintained between the fixed gripping tool and the moveable gripping tool. This distance should be maintained in order to avoid applying tension or compression to the wire. Since the moveable gripping tool is moving potential in three dimensions during the bending, the distance that needs to be maintained is measured along the length of the archwire. The same principle holds true for bending other types of devices.

These and still other aspects of the invention will be more apparent in view of the following detailed description of a presently preferred embodiment.

BRIEF DESCRIPTION OF THE DRAWINGS

FIG. 2 is a schematic representation of an archwire manufacturing system shown in FIG. 1.

in FIG. 3 the gripping tool at the distal end of the arm is omitted for sake of clarity to show the various other aspects of the arm.

FIG. 18 shows in matrix form the values for an individual bracket which describe the location of the bracket and its orientation, which are used to generate the commands for the robot to form the orthodontic archwire.

FIG. 19 is an illustration of a set of points P1, P2, P3, ... PN which represent a set of bending points associated with individual brackets for a patient in a target situation. The location of the points in the three-dimensional coordinate system is known.

FIG. 20 is an illustration of a section of wire between points P1 and P4 in which a bend is placed between points P2 and P3.

DETAILED DESCRIPTION OF A PREFERRED EMBODIMENT

Part 1. Overview

Figure 1:
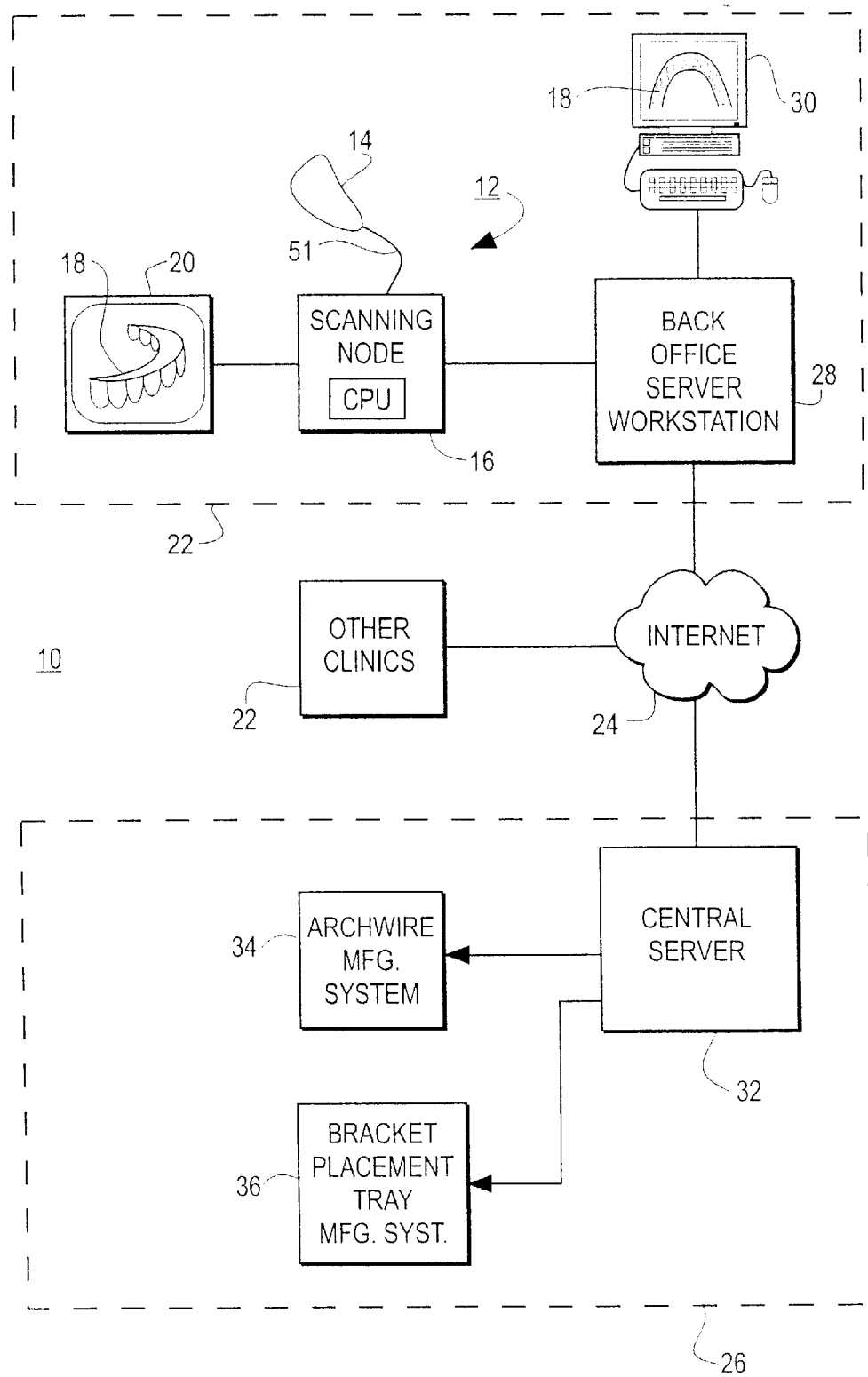
FIG. 1 is an illustration of an orthodontic care system incorporating a hand-held scanner system and an archwire manufacturing system in accordance with a representative embodiment of the invention. The hand-held scanner is used by the orthodontist to acquire three-dimensional information of the dentition and associated anatomical structures of a patient and provide a base of information to plan treatment for the patient. The archwire manufacturing system includes a wire bending robot to manufacture customized orthodontic archwires for shipment to the clinic.

FIG. 1 is an illustration of an orthodontic care system 10 incorporating a hand-held scanner system 12. The scanner system 12 includes a hand-held scanner 14 that is used by the orthodontist to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information to plan treatment for the patient. The model 18 is displayed to the user on a monitor 20 connected to the scanning node 16.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user interface, including a monitor 30. The back office server 28 executes an orthodontic treatment planning software program. The software obtains the three-dimensional digital data of the patient's teeth from the scanning node and displays the model 18 for the orthodontist. The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket position. When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22.

As shown in FIG. 1, the precision appliance service center 26 includes a central server 32, an archwire manufacturing system 34 and a bracket placement manufacturing system 36. The details of the scanning system per se are not particularly relevant to the wire bending features of the invention and are therefore omitted from the present discussion for sake of brevity except to the extent relevant to the present invention. For more details on these aspects of the illustrated orthodontic care system, the interested reader is directed to the patent application of Rudger Rubbert et al., filed Apr. 13, 2001, entitled INTERACTIVE AND ARCH WIRE-BASED ORTHODONTIC CARE SYSTEM BASED ON INTRA-ORAL SCANNING OF TEETH, Ser. No. 09/835,039, now U.S. Pat. No. 6,648,640, the contents of which are incorporated by reference herein, and the patent application of Rüdger Rubbert et al., SCANNING SYSTEM AND CALIBRATION METHOD FOR CAPTURING PRECISE THREE-DIMENSIONAL INFORMATION OF OBJECTS, Ser. No. 09/834,593, also filed on Apr. 13, 2001, the contents of which are incorporated by reference herein.

Part 2. Archwire Manufacturing System

A. Robot Design

Figure 2A:
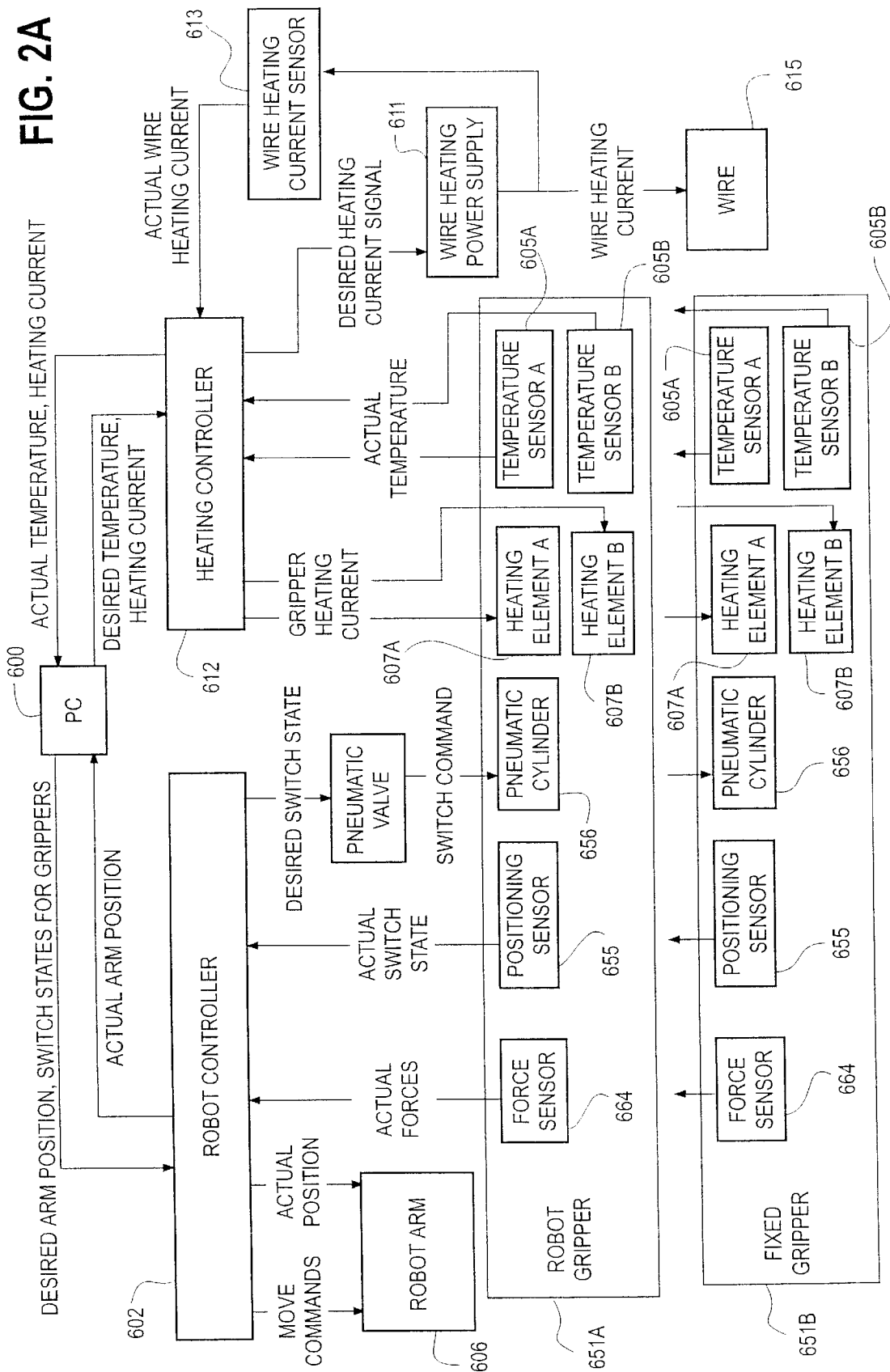
FIG. 2A is a block diagram of the system.

FIG. 2 is a schematic representation of a presently preferred archwire manufacturing system 34 shown in FIG. 1. The key aspects of the system 34 are shown in block diagram form in FIG. 2A. The system 34 includes a control system for controlling the operation of a wire bending robot 604. The control system in the illustrated embodiment comprises a general purpose computer 600 running a bending program and a robot controller 602. The computer 600 receives an input file from the precision appliance service center computer that contains information as to the location of bracket slots in three dimensions, when the teeth are in a target situation. The computer 600 supplies the robot controller 602 with wire position information corresponding to points along the wire where bends need to be made. This information is translated by the controller 602 into motion commands for the wire bending robot 604.

It will be appreciated that the system works in an analogous fashion when bending other types of medical devices. The computer 600 receives an input file from some source that provides information as to how the medical device in question needs to be bent. The computer 600 supplies the robot controller 602 with position information corresponding to points along the length of the medical device where bends need to be made, and the robot responsively bends a medical device in accordance with the input file.

The wire bending robot 604 consists of a moveable arm 606 having a gripping tool at the distal end thereof. The moveable arm has a proximal end mounted to a table or base 610. The robot also includes a first gripping tool 608. In the illustrated embodiment, the first gripping tool 608 is fixed with respect to the base 610 and mounted to the table. Hence, the first gripper tool 608 will be referred to herein occasionally as the "fixed gripper." It would be possible to place the first gripper tool 608 at the end of second robot arm, in which case the first gripper tool would not necessarily be fixed, but rather would be free to move in space relative to the source of archwires, or the other moveable arm. In such as system, a coordinate system would be defined having an origin at which the first tool is positioned at a known position. The bending commands for the robot would be with respect to this known point.

A wire or other workpiece to be bent is held by the first gripper 608 and the gripping tool at the end of the moveable arm 606, and the arm is moved to a new position in space to thereby bend the workpiece. The details of the construction of the arm 606 and fixed gripper 608 are described in further detail below.

Figure 7:
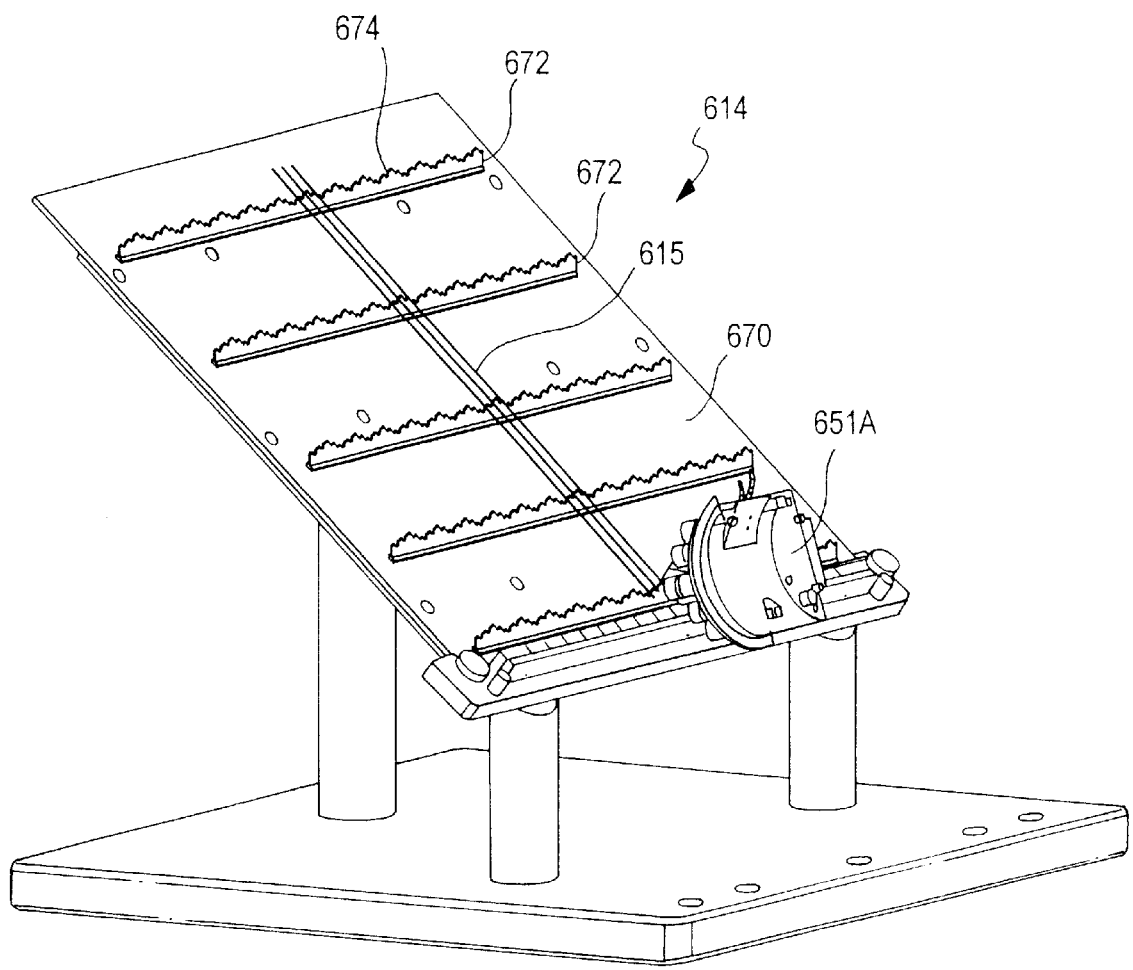
FIG. 7 is a perspective view of a magazine of FIG. 2 that holds a plurality of straight archwires.

The system 34 of FIG. 2 is set up to manufacture customized archwires one after the other continuously, as would be case in a precision appliance service center serving a plurality of clinics. As such, the robot 604 includes a source of archwire material. The source could be a spool of wire in which case a cutting tool is needed to cut lengths of wire for individual archwires. Alternatively, as shown in FIG. 2 and 7 the source consists of a magazine 614 containing a plurality of straight archwires 615 ready to be grasped by the gripping tool at the end of the moveable arm 606. In an embodiment in which the first gripping tool is mounted to the end of a moveable arm, the first gripping tool could retrieve the next workpiece while the moveable arm places the finished workpiece at an exit location.

After an archwire is bent in accordance with an input file supplied to the computer 600, the moveable gripping tool at the end of the robot arm 606 places the wire (or workpiece being bent) at an exit location indicated at 616. A conveyor system 618 including a plurality of trays 620 is provided for carrying the finished archwires wires 622 from the exit location 616 to a labeling and packaging station 624. The labeling and packaging station 624 includes a printer 626 that prints a label for the archwire and a magazine 628 containing a supply of packages such as boxes or bags for the wires. A worker at the station 624 takes a label from the printer and applies it to the archwire 622 or to the package for the wire. The conveyor system 618 is also based on a commercially available, off-the-shelf conveyor system, such as of the type available from the Montech division of Montrac.

The wire manufacturing system 34 includes a heating controller 612 responsive to commands and settings from the wire manufacturing computer 600. The controller 612 controls the supply of current to heating elements 607A and 607B in the gripping fingers in the gripping tools in the robot, to thereby heat the gripping fingers above ambient temperature. Temperature sensors 605A and 605B detect the temperature of the gripper fingers and are used for feedback control of the heating of the gripper fingers. A direct or indirect system for measuring the temperature of the workpiece may also be provided, such as infrared heat detector. The heating controller 612 also controls a wire heating power supply 611 that supplies a current to the gripping tools when they are bending a wire. The power supply 611 is used when the robot is bending shape memory materials or Titanium Molybdenum Alloys (TMA) materials, or possibly other materials. The current produces a resistive heating in the wire. The current is controlled via a wire heating current sensor 613 so as to produce a wire temperature at which a bend formed in the wire is set into the material. The heating of the gripping fingers avoids excessive heat loss when resistive heating of the wire is performed.

Figure 3:
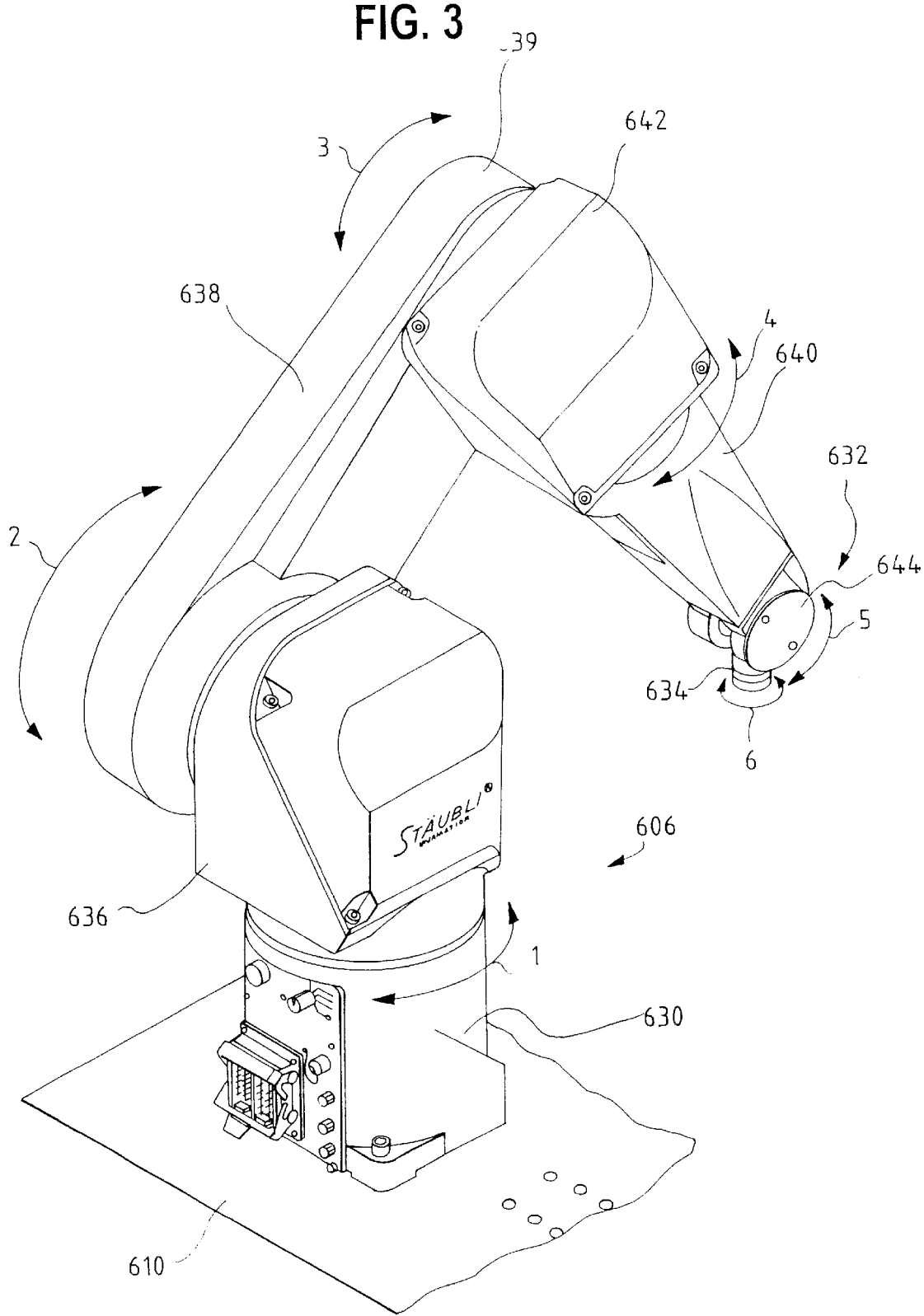
FIG. 3 is a perspective view of a moveable robot arm used in the manufacturing system in FIG. 2.

FIG. 3 is a perspective view of a moveable robot arm 606 used in the manufacturing system in FIG. 2. In FIG. 3, the gripping tool at the distal end 634 of the arm is omitted. In a preferred embodiment, the moveable arm is based on an off-the-shelf six-axis robot arm and fixed tool. A suitable arm, fixed tool, and robot controller for the robot 604 is available from Staubli Unimation of Germany. The Staubli robot arm and fixed tool is customized with gripping fingers, heating controller and ancillary systems, software, current heating subsystem, force sensors, and other features as described herein for bending archwires or other suitable medical devices.

Figure 6:
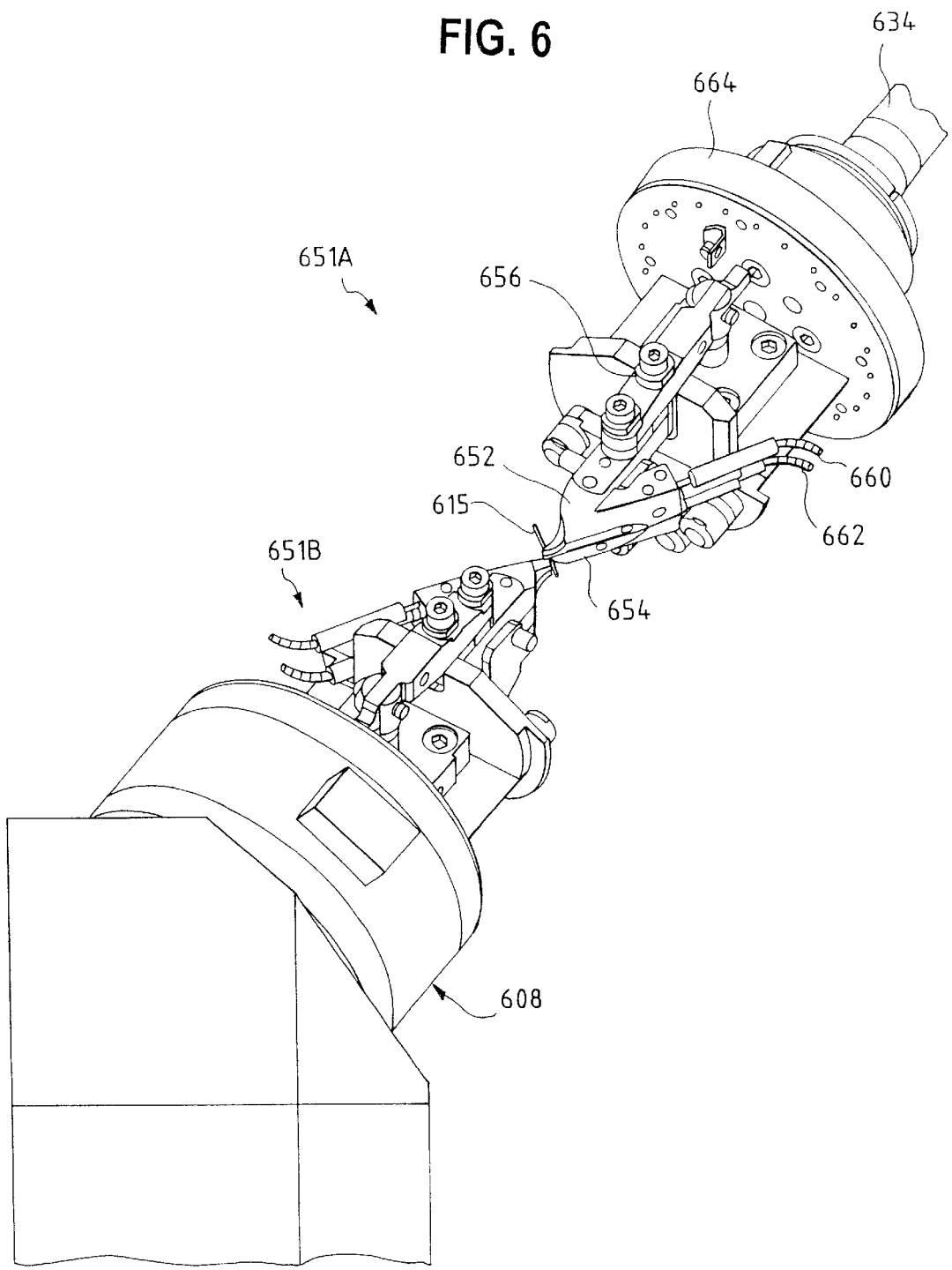
FIG. 6 is a perspective view of the fixed gripping tool of FIG. 2 and the gripping tool of FIG. 5, in which an orthodontic archwire is gripped by the tools.

The arm 606 consists of a proximal end or base 630 which mounts to the table 610 of FIG. 2 and a free distal end 632 consisting of a tool flange 634, where the second gripping tool 651A of FIG. 6 is mounted, as described below. The arm 606 is capable of motion along six different rotational axes, with the directions indicated by the arrows numbered 1–6 in FIG. 3. Thus, the base is fixed with respect to the table 610 and the head portion 636 rotates relative to the base 630. A joint in head portion 636 rotates arm segment 638 about an axis indicated by arrow 2. Similarly, the arm segment 640 is rotated about an axis indicated by arrow 3 by a joint 639. A joint 642 rotates an arm segment 640 about the axis indicated by the arrow 4. A joint 644 attached to the end of arm segment 640 rotates the tool flange 634 about the axis indicated by arrow 5. A sixth joint (not shown) rotates the tool flange 634 about an axis indicated by arrow 6.

Figure 4:
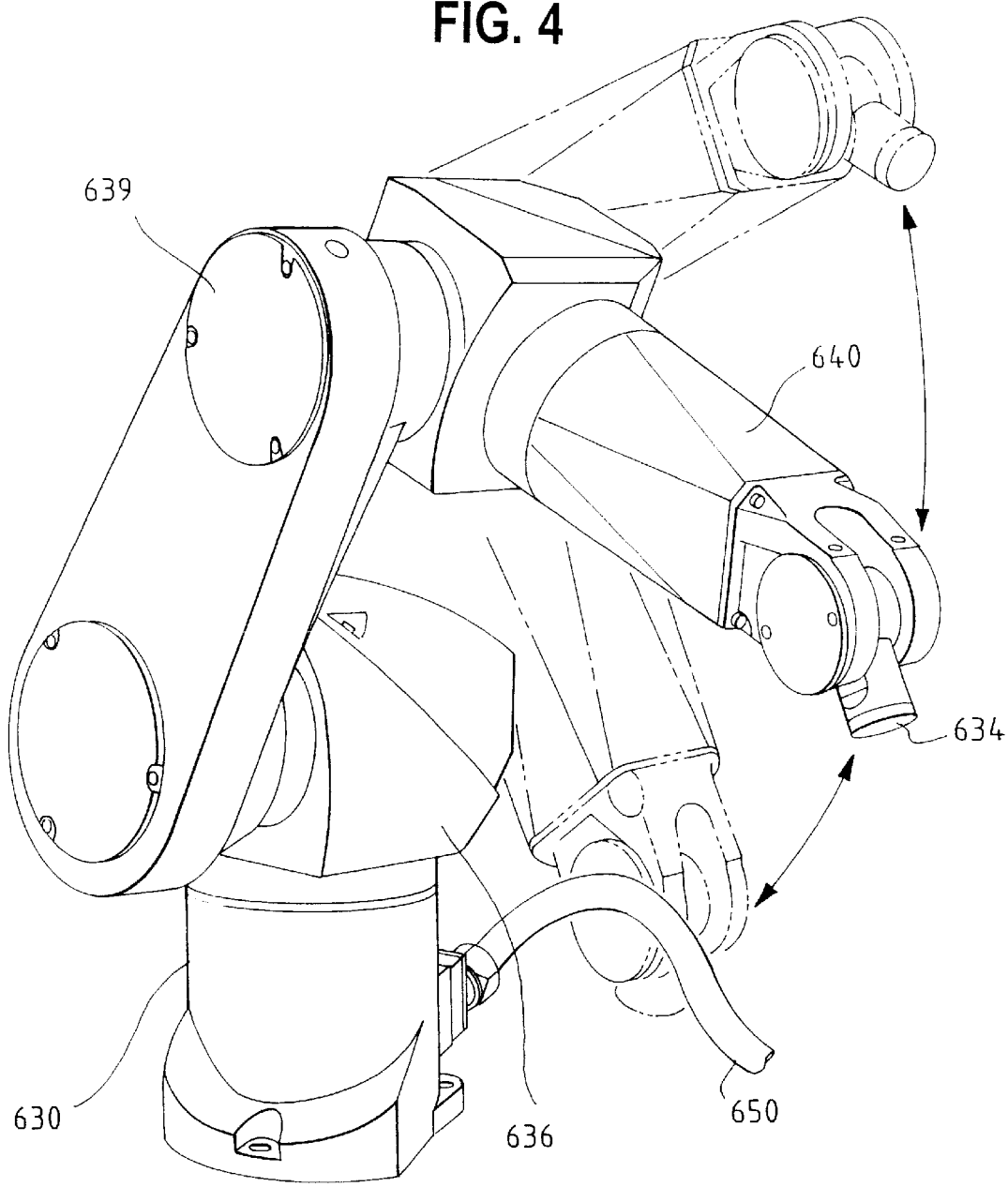
FIG. 4 is perspective view of the robot arm of FIG. 3, showing the movement of one of the arm joints and the corresponding motion of the arm.

FIG. 4 is perspective view of the robot arm of FIG. 3, showing the movement of the arm joint 639 and the corresponding motion of the arm segment 640 and tool flange 634. The motion commands for the robot are supplied from the robot controller 602 along a cable 650 which plugs into the base 630 of the robot.

Figure 5:
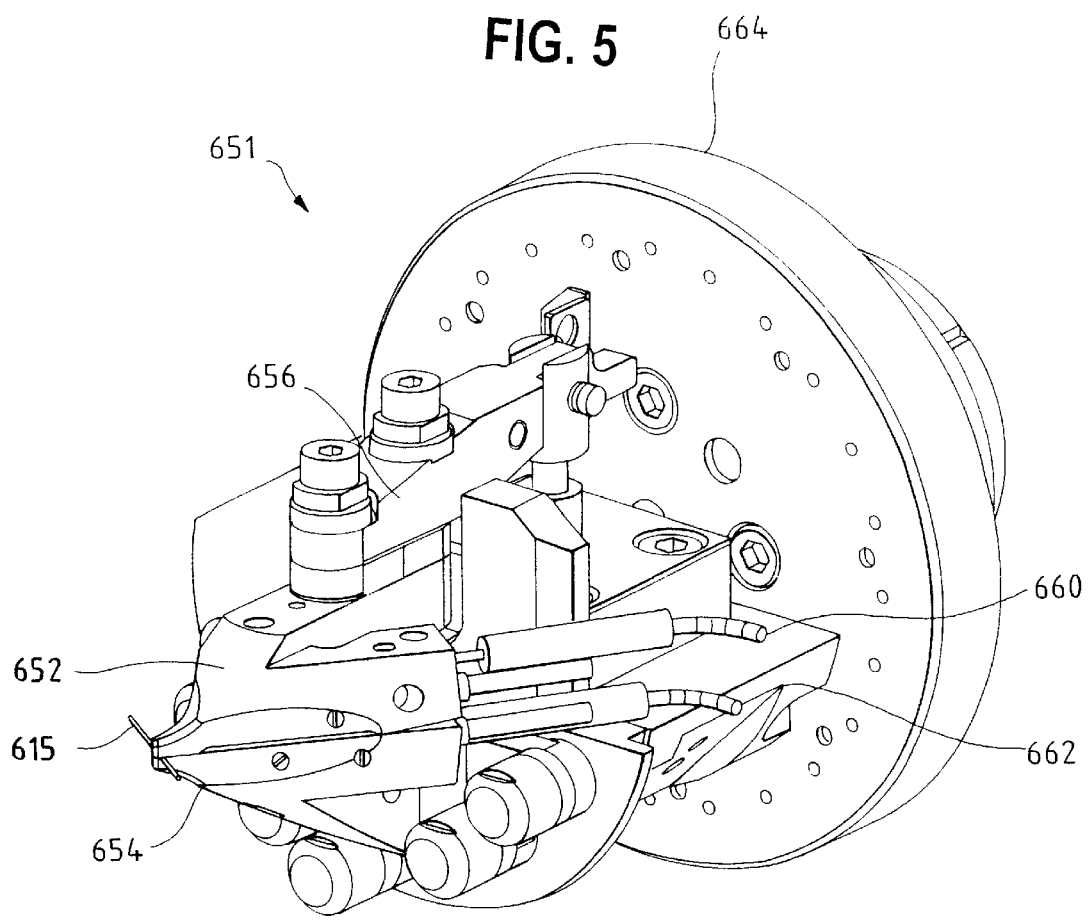
FIG. 5 is a detailed perspective view of the gripping tool that is mounted to the distal end of the moveable robot arm of FIG. 3 and FIG. 4.

FIG. 5 is a detailed perspective view of a preferred gripping tool 651A that is mounted to the tool flange 634 at the distal end of the robot arm 606 of FIG. 3 and FIG. 4. The construction shown in FIG. 5 also applies to the fixed gripper 608 of FIG. 2 and FIG. 6. The gripping tool 651A consists of a pair of opposed gripping fingers 652 and 654 which open and close to grip and release the workpiece, in this case an orthodontic archwire 615. A pneumatic cylinder actuates gripping finger 652 by moving it about an axis relative to finger 654, to thereby permit the fingers 652 and 654 to grip and release a workpiece such as a wire. A positioning sensor 655 (FIG. 2A) detects the position of the fingers.

In a representative embodiment, the archwires are made from a shape memory alloy such as Nitinol, a material based on Nickel and Titanium plus Copper or other alloy. These materials can be heated to retain the shape of a bend formed in the wire. Accordingly, the wire heating power supply 611 of FIG. 2A supplies a current to the gripping fingers of the fixed gripping tool and the moveable gripping tool. The flow of current along the wire creates a resistive heating of the wire sufficient for the material to take a set according to the shape of the wire as it is bent. To avoid dissipation of heat from the wire into the gripping fingers, the gripping fingers 652 and 654 are preferably heated by electrical heating elements 607A and 607B. Conductors 660 and 662 supply current to the heating elements in the gripper fingers.

The gripping tool 651A of FIG. 5 further includes a force sensor 664 in the form of a strain gauge. The force sensor is designed to detect forces that the wire imparts to the gripping fingers after a bend has been placed in the wire or during the bending movement. The forces detected by the force sensor 664 are determined both in magnitude and in direction in three-dimensions. The use of the output from the force sensors to overbend wire is explained in further detail below.

FIG. 6 is a perspective view of the fixed gripper 608 having a gripper tool 651B as shown in FIG. 5 along with a moveable gripping tool 651A located at the distal end 632 of the moveable arm 606. An orthodontic archwire 615 is shown gripped by the gripping tools 651A and 651B. The fixed gripper 608 and gripping tool 651B remain stationary relative to the base 610. The archwire is bent or twisted by the fixed gripping tool 651 grasping the archwire 615 and the moveable gripping tool 651A also grasping the archwire 615, and then moveable gripping tooling 651A bending the wire by moving to a new location in three-dimensional space relative to the fixed gripping tools. The location in space for the moveable arm to move to is determined by the input file fed to the robot computer 600. Basically, the input file consists of a series of point locations in a three dimensional coordinate system which correspond to bracket locations and orientation in a three-dimensional coordinate system for the arch, as described in more detail below. The manner of calculation of these points and generating movement commands (i.e., arm position and switch states for the gripper fingers) for the robot's moveable arm and commands for the fixed gripper to bend the wire will be described in further detail below.

Other possibilities exist for input files and calculation of the bending points. For example, in extraction cases, the wire is needed to close a gap between teeth and the wire serves as a guide or rail for the bracket to slide along to close the teeth. In this situation, a smooth curve is needed between the teeth to allow the brackets to slide the required amount. In this situation, the space between the teeth is divided into small sections, and wire coordinates are obtained for each section. A series of small bends are formed at each section to generate the required smooth curve. It may be helpful in this situation to round the edges of the gripping fingers to help provide the desired smooth shape. As another alternative, free-form curves can be formed by bending the wire between two points which would encompass a plurality of brackets.

While the preferred embodiment of a robot arm is shown in FIG. 3, that is not the only possible arrangement of a robot arm. The robot of FIG. 3 is optimized for complex bends and twists in archwires. However, some medical devices or archwires may need only simple bends, in which case a lesser number of joints may be required. For example, a one, two or three axis robot may be sufficient for some applications.

Figure 9:
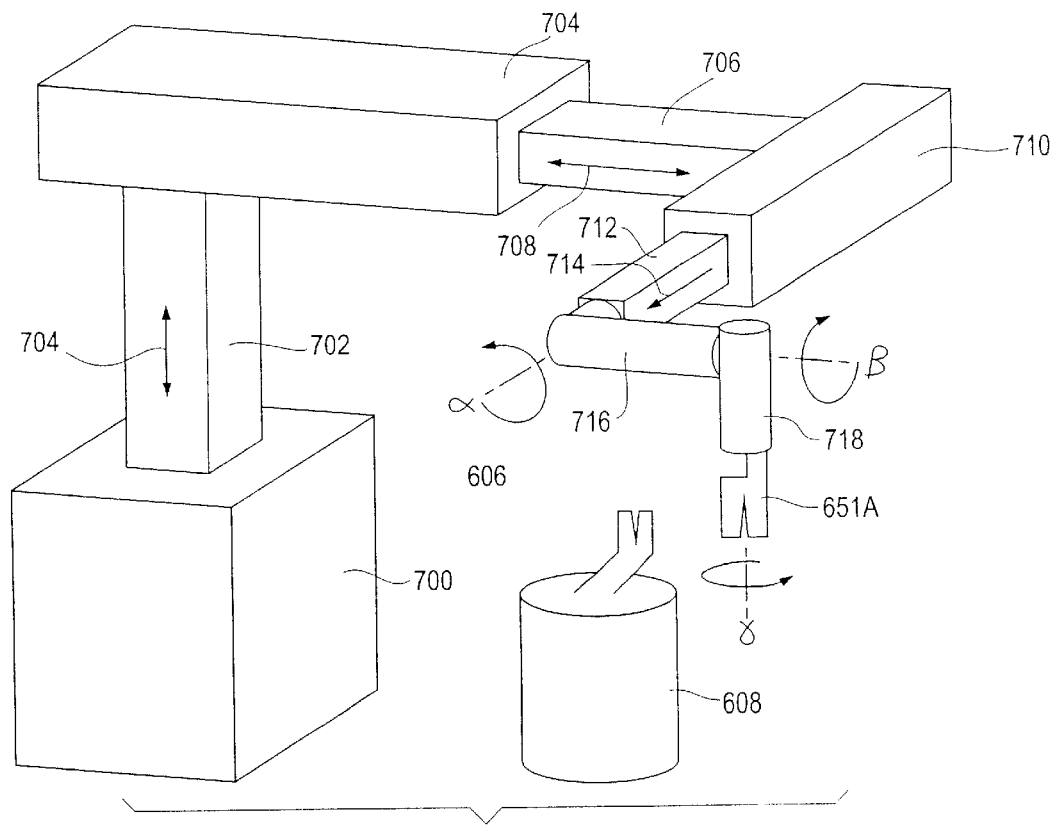
FIG. 9 is a perspective view of an alternative arrangement of a moveable robot arm.

FIG. 9 is a perspective view of an alternative arrangement of a six-axis moveable robot arm. In this embodiment, the robot arm comprises a base 700, a motor that moves arm segment 702 along direction 704, a second section that contains a motor that moves second arm segment 706 along direction 708, and a third section 710 that contains a motor moving the arm section 712 along direction 714. A motor is provided for rotating arm section 712 about axis α. A section 716 is connected to the end of section 712 and includes a motor for rotation of section 716 about an axis indicated by β. A sixth section 718 is rotated about an axis indicated by γ. The gripping tool 651 A is mounted to the end of the section 718. Robots of this type are also known and suitable for forming the basis of an orthodontic archwire bending robot. The term "moveable arm" as used in the claims is intended to interpreted broadly to encompass the arm segments of the type shown in FIG. 9 as well as the construction shown in FIG. 4.

The gripping fingers of the gripping tools 651A and 652 preferably optimized, in terms of their physical configuration, for the type and shape of the workpiece being bent. This shape may change depending on the nature of the workpiece, e.g., wire, fixation plate, spectacle frames, etc. In the case of wires, wires come in various cross-sections and sizes. It may be desirable to form a plurality of contours in the gripping fingers so as to enable the gripping fingers to grip several different types and sizes of wires without changing gripping tools. For example, one part of the gripper fingers has a series of rectangular contours to grip wires of rectangular cross-section of varying sizes, and perhaps one or more circular contours to grip round wires.

The force sensors on the gripping tools may also be used to provide feedback for an adjustable gripping force to be applied to the workpiece (e.g., wires). It may be desirable to allow the wire to slide through the gripper fingers if the forces acting from the workpiece to the gripper exceed a certain limit. When these forces are sensed, the fixed gripper loosens its grip on the workpiece and allows it to slide.

Figure 8:
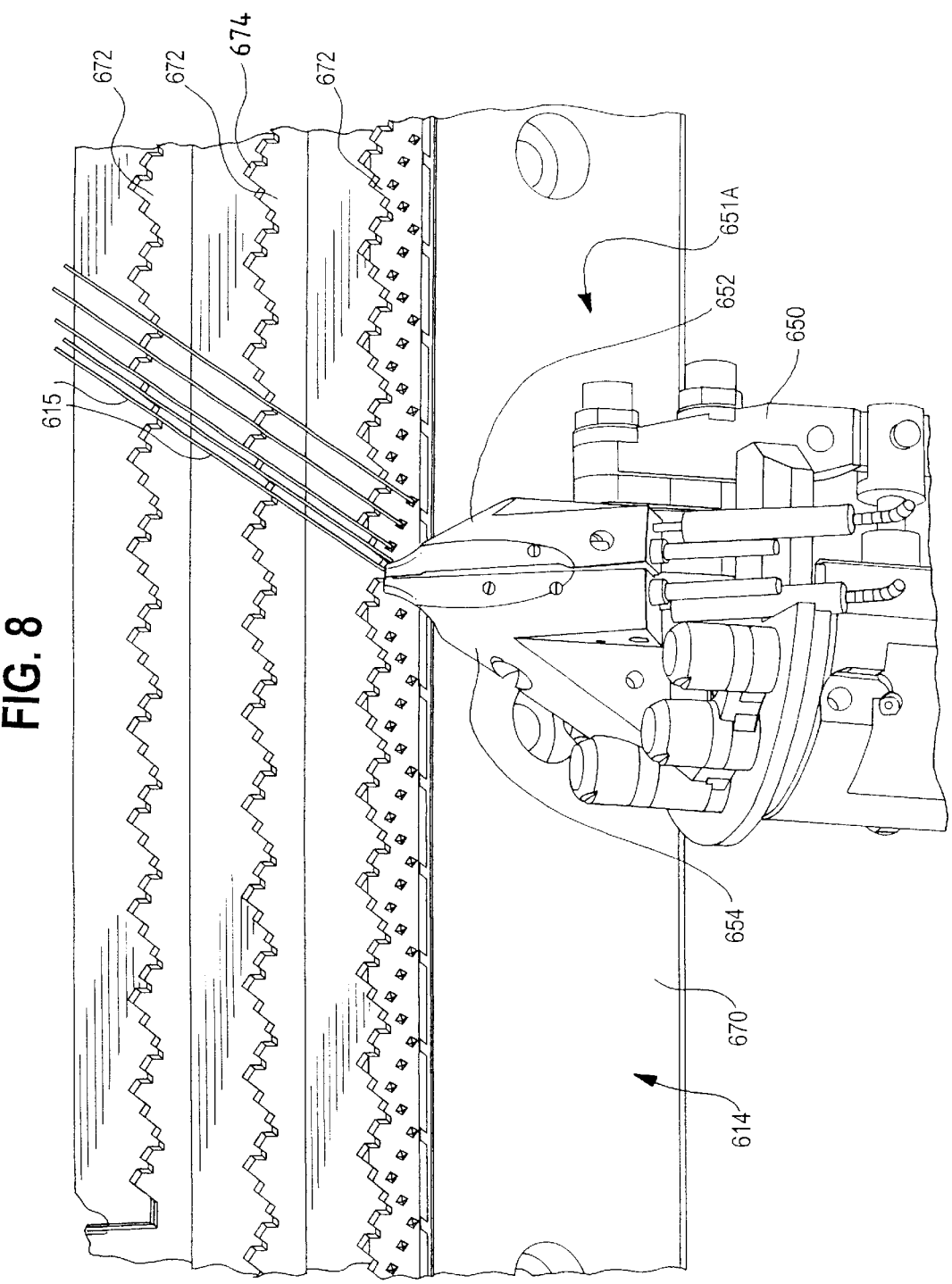
FIG. 8 is a detailed perspective view of the moveable gripping tool grasping one of the archwires from the magazine of FIG. 7.

FIG. 7 is a perspective view of a magazine 614 of FIG. 2 that holds a plurality of straight archwires needing to be bent in an presently preferred embodiment. FIG. 8 is a detailed perspective view of the moveable gripping tool grasping one of the archwires from the magazine of FIG. 7.

The magazine 614 consists of a tray 670 having a set of parallel raised elements 672 that define a series of grooves 674 in the upper surface thereof. The archwires 615 are placed in the grooves 674. The archwires are maintained spaced apart from each other in the tray. This permits the robot's moveable gripping tool 651A to pick up a single archwire at a time from the magazine 614 as shown in FIG. 8 and insert it into the fixed gripping tool to commence a bending operation. Also, the magazine 614 is positioned at a known location and the dimensions of the tray and slot features thereof are known precisely. This location information is supplied to the robot control software and allows the gripping tool 651A to remove the archwires one at a time from the magazine automatically and without human assistance. When the magazine 614 is empty a full one is placed at the same location.

Figure 10A:
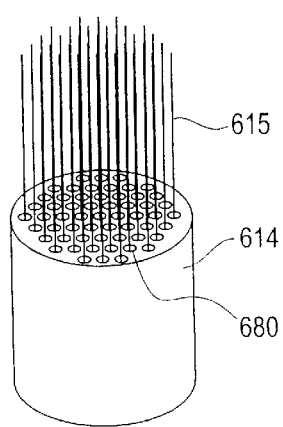
FIGS. 10A and 10B are perspective views of alternative magazine constructions to the magazine of FIG. 7.
Figure 10B:
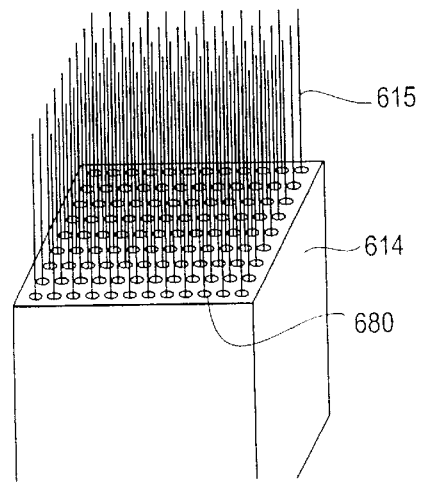

FIGS. 10A and 10B are perspective views of alternative magazine constructions to the magazine of FIG. 7. In FIG. 10A, the magazine 614 consists of a cylindrical holder with a plurality of apertures 680 spaced from each other, each containing a straight archwire 615. In FIG. 10B, the archwires are in a rectangular holder with the apertures arranged in rows and columns. In either case, the moveable arm grips an individual one of the archwires and removes it from the magazine by virtue of the spacing of the wires from each other in the magazine and because the location of each wire in the magazine can be known.

Figure 11:
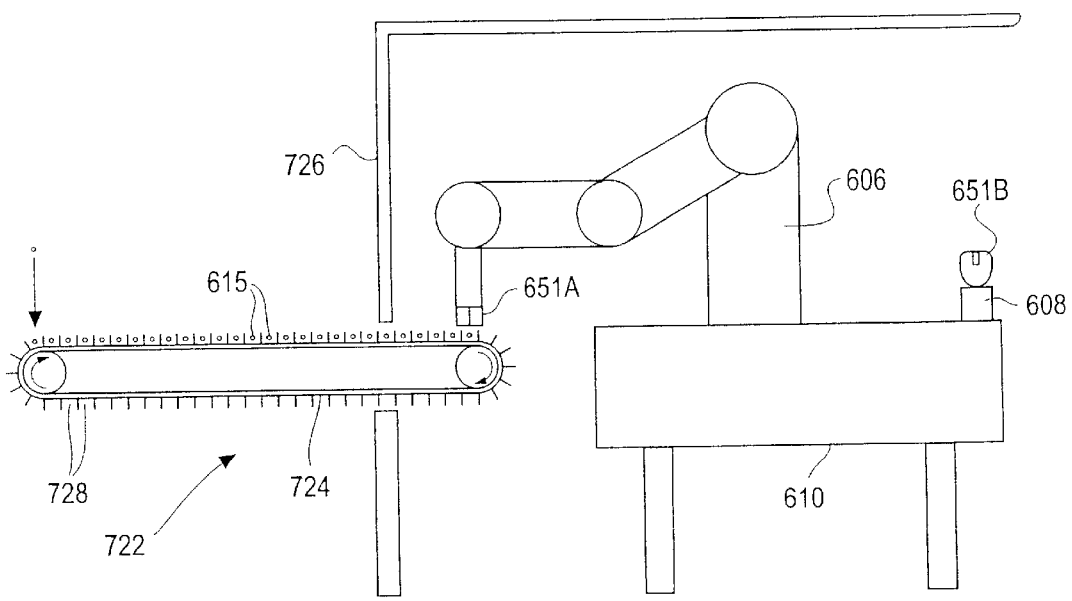
FIG. 11 is a schematic illustration of a conveyor system that carries archwires to the robot arm of FIG. 2.

FIG. 11 is a schematic illustration of a conveyor system 722 including a conveyor belt 724 that carries archwires 615 to the robot. Here, the robot is enclosed within a safety cage 726. A source feeds archwires 615 into slots 728 in the conveyor belt. When a wire has been bent and the robot is ready for a new wire, the belt advances one position and the robot grips the next wire placed on the belt 724. As another alternative, a spool of archwire can be fed to the robot and a cutting tool (not shown) provided for cutting the wire from the spool into a desired length. The cutting tool could be incorporated into the end of a second robot arm, for example. Still further implementations are possible.

It also possible for the archwire manufacturing system to have other workstations or workplaces in which one or more of the following tasks may be performed: loop bending, surface refining, and marking of the wires. These stations could be positioned at locations around the conveyor system 722 or be in separate locations.

It is also possible to enclosed the robotic wire bending system within an enclosure and fill the enclosure with an inert gas such as nitrogen. The inert gas prevents oxidation of the workpiece during bending or oxidation or other chemical reaction affecting the gripping tools.

Appliance Manufacturing

Figure 12:
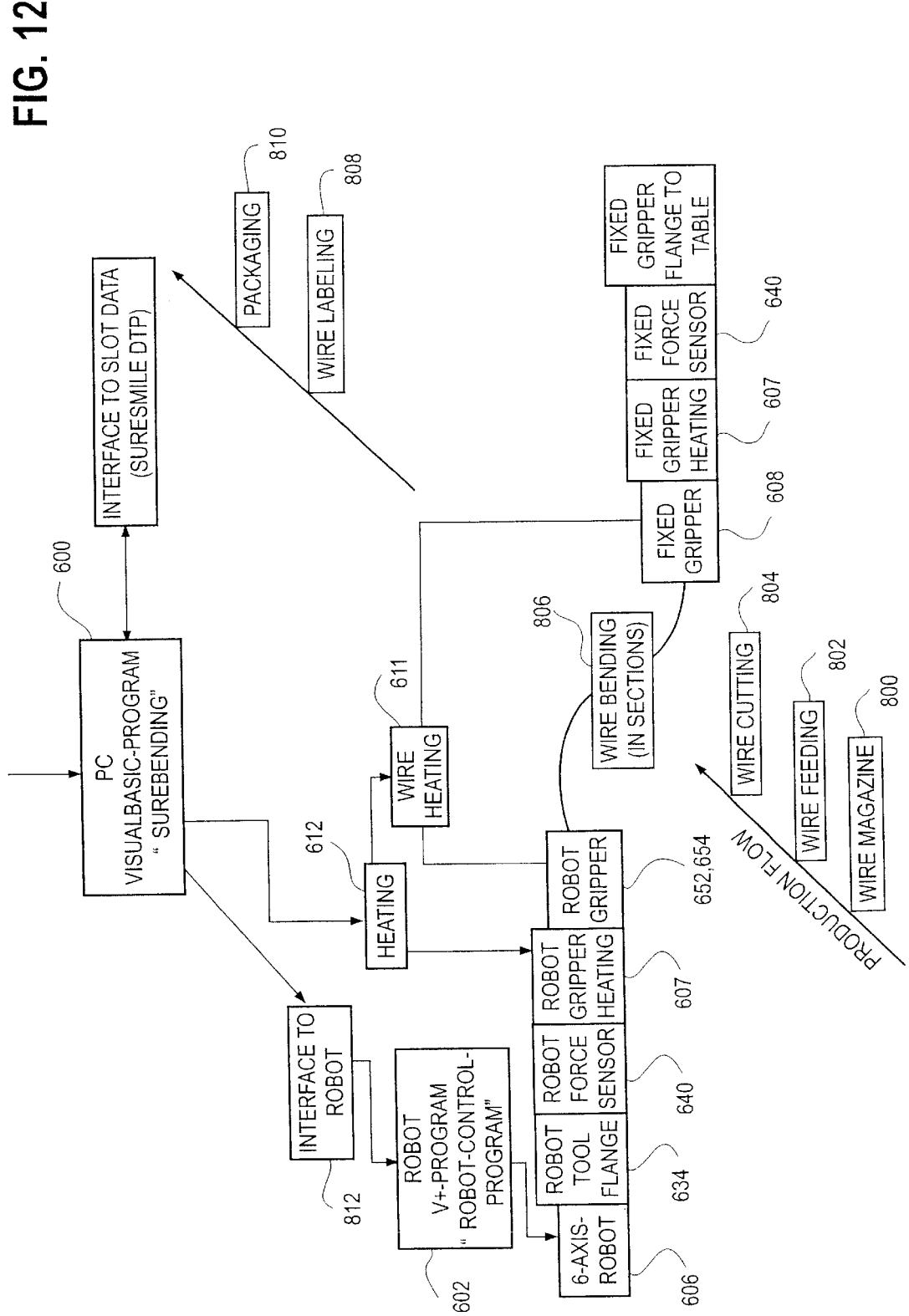
FIG. 12 is a diagram illustrating the robot software as it relates to the production flow in producing orthodontic archwires.

The production flow for manufacturing archwires (or other similar appliances) with a representative embodiment of the wire manufacturing system of FIG. 2 is shown in FIG. 12. The production flow includes the step 800 of loading a wire magazine 614, such as spool of wire in an alternative embodiment, feeding the wire to the robot at step 802 and cutting the wire to length at step 804. At step 806, a series of bends are placed in the archwire in accordance with the prescription for the archwire. After the bending is complete, the wires are labeled at the station 624 at step 808 and packaged in a box or other package at step 810.

The bending of the wire at step 806 is based on slot data for bracket slots at described below in conjunction with FIGS. 13–20, or based on some other suitable criteria as explained herein. The wire bending computer 600 receives this slot data from the precision appliance center computer of FIG. 1. The computer 600 executes a bending program that processes the slot data into a set of points in three dimensional space and calculates movements of the moveable arm necessary to achieve the appropriate bends in the wire. The computer 600 has a software interface 812 to the robot controller, which translates position or movement signals for the robot arm into low level instructions for the robot controller 602. The robot controller executes a robot control program (adapted from the control program that comes with the robot) which causes the robot arm 606 to move relative to the fixed gripper 608 to bend and/or twist the wire. Where the archwire is a shape memory alloy, the wire heating power supply 611 supplies current to the gripper fingers 652 and 652 on the moveable arm and the gripper fingers on the fixed gripper 608 to heat the wire while the wire is held in the bent condition, and/or during bending motion, to set the shape of the wire.

Robot Input File

The input file, which dictates the shape of an archwire after bending, will now be discussed in conjunction with FIGS. 13–20. The input file includes a set of matrices, one matrix for each bracket in the arch of the patient. Each matrix consists of a combination of a vector of location of a point on the bracket and a matrix of orientation, indicating the orientation of the bracket in three-dimensional space. Both the vector of location and the matrix of orientation are based on the position of the brackets on the teeth when the teeth are in a target situation. The target situation is developed by the orthodontist from the scan of the dentition and the execution of a treatment planning using the treatment planning software at the clinic.

Figure 13:
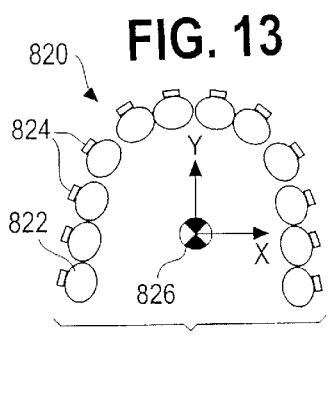
FIG. 13 is a simplified illustration of a set of teeth showing the origin of a coordinate system that is used to calculate bracket location for a set of brackets, in three dimensions, for a patient. The bracket location for the teeth in a target situation determines the shape of an orthodontic archwire.

FIG. 13 illustrates the target situation for one arch 820 a patient. The target situation is a three dimensional virtual model of the teeth 822 in which virtual brackets 824 are placed, for example, on the labial surface of the teeth. A coordinate system is defined for the arch 820 having an origin 826. The coordinate system is in three dimensions, with the X and Y dimensions lying in the plane of the arch and the Z direction pointing out of the page. The location of the origin 826 is not particularly important. In the illustrated embodiment, an average "mass" is assigned to each virtual tooth in the arch, and a center of "mass" is calculated for the arch 820 and the original 826 is located at that center.

Figure 14:
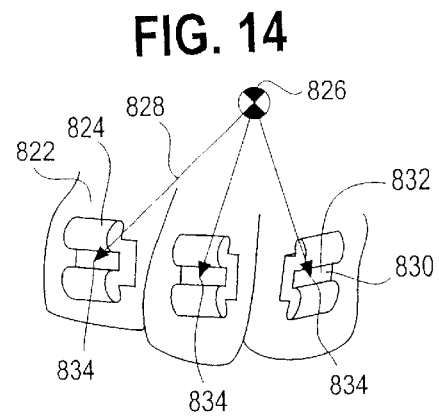
FIG. 14 is an illustration showing the vectors drawn from the origin of the coordinate system to the center of the brackets.
Figure 15:
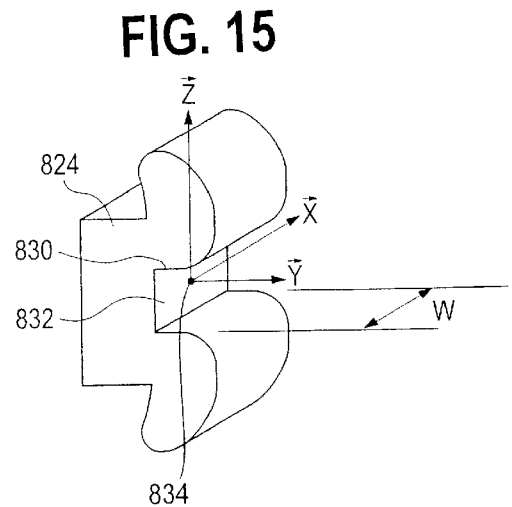
FIG. 15 is a perspective view of an orthodontic bracket.

As shown in FIGS. 14 and 15, a vector of location 828 is defined for each bracket. The vector 828 extends from the origin 826 to the center of the slot 830 in the bracket along the wall 832 of the bracket slot, i.e., to point 834. The vector of location consists of the X, Y and Z coordinates of the point 834 in the defined arch coordinate system.

The orientation matrix consists of a 3×3 matrix of unit vectors of the form:

$$\begin{matrix} X_1 & Y_1 & Z_1 \\ X_2 & Y_2 & Z_2 \\ X_3 & Y_3 & Z_3 \end{matrix} \quad 1)$$

where $X_1$ $X_2$ and $X_3$ are the X Y and Z components of the X unit vector shown in FIG. 15, $Y_1$ $Y_2$ and $Y_3$ are the X, Y and Z components of the Y unit vector shown in FIG. 15, and $Z_1$ $Z_2$ $Z_3$ are the X, Y and Z components of the Z unit vector shown in FIG. 15. As noted above, the matrix for each bracket thus consists of the combination of the 3×3 orientation matrix and the position matrix, and is thus as follows:

$$\begin{matrix} X_1 & Y_1 & Z_1 & X \\ X_2 & Y_2 & Z_2 & Y \\ X_3 & Y_3 & Z_3 & Z \\ 0 & 0 & 0 & 1 \end{matrix} \quad 2)$$

where X, Y and Z in the right hand column of entries is the position vector.

The robot input file also includes an antitangential value and a tangential value for each bracket. The antitangential value consists of the distance from the center of the bracket slot (point 834) to a point defining the terminus of the previous bend in the wire. The tangential value consists of the distance from the center of the bracket slot to the point defining the terminus of the next bend in the wire. The input file also consists of the thickness of the wire, as measured in the direction of the Y unit vector in FIG. 15.

Figure 16:
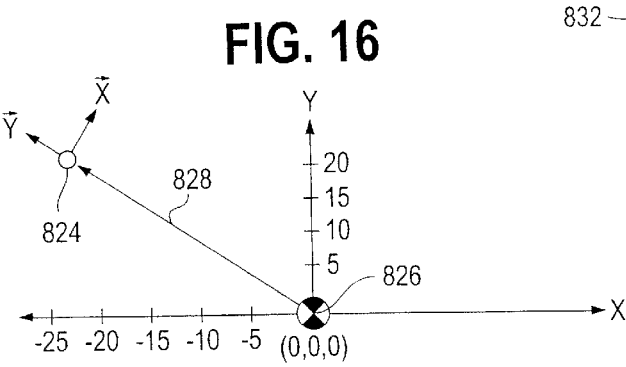
FIG. 16 is an illustration of a vector drawn from the origin of the coordinate system to the bracket, a normal vector N perpendicular to the slot surface of the bracket, and a tangential vector T extending in the direction of the slot of the bracket.
Figure 17:
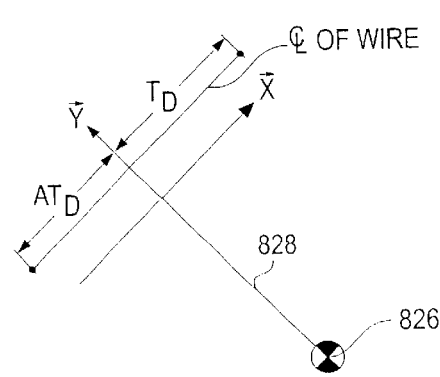
FIG. 17 shows the normal vector Y for a particular bracket, the tangential vector X, the tangential distance $T_d$ and antitangential distance $AT_d$.

With reference to FIG. 16, an example of the 4×4 matrix 2) for a rear most molar of a patient will be described. Figure shows the origin 826, the position vector 828, and the X and Y unit vectors which indicate the orientation of the bracket slot. FIG. 16 also shows the scale (in units of millimeters) which gives absolute location and orientation information for the bracket slot. Here, we assume in the example that there is no Z component to the tangential vector X or the normal vector Y. FIG. 17 shows the tangential distance $T_D$ and the antitangential distance $AT_D$ as measured along the centerline of the archwire. The resulting matrix is shown in FIG. 18.

From a set of the matrices as shown in FIG. 18 comprising all the brackets in the arch, the robot bending program extracts a series of line segments in three dimensional space, which are defined by the terminus of the antitangential and tangential distances for each bracket slot. The set of line segments 840 is shown in FIG. 19. The line segments are defined by a set of points P1, P2, P3 . . . Pn having known three dimensional coordinates due to the known location of the bracket slots and the known tangential and antitangential distances. The line segments can also be defined as a set of vectors having a location for the head of the vector and a magnitude and orientation in three directions. The following discussion will use the set of points P1, P2, P3 . . . PN. In FIG. 19, the slashes 842 indicate the end points of the bracket slot 830 of FIG. 15.

The bends need to be placed in the wire before point P1, between points P2 and P3, between points P4 and P5, etc., that is, between the bracket slots. The slot-to-slot bends of the complete archwire are bent section by section. To form one slot-to-slot bend, the wire is fed so that the fixed gripper tool 651B and the robot arm gripper tool 651A can grip the wire in its initial shape. The wire length between fixed gripper and robot arm gripper is equal to the curved length of the wire along the bend. The straight wire sections 840 between the bends have to fit to the bracket slots. To bend the wire into the demanded shape, the main control computer 600 sends signals to the robot controller 602. The robot controller 602 generates signals to move the robot arm 606 with the robot gripper tool 651A into a new position. The movement path is defined by a bending trajectory. The bend is indicated at 844 in FIG. 20.

To form one slot-to-slot bend (e.g., bend 844 between P2 and P3), there might be several of these bending movements necessary. One slot-to-slot bend is considered finished if two consecutive straight wire sections (e.g., between P1 and P2 and between P3 and P4), have the desired relative positions between one another.

To achieve this position, there are different approaches dependent on the wire material properties possible: a) bending material with elastic/plastic properties, such as stainless steel, b) bending material with shape memory properties, and c) bending TMA alloys.

Material with elastic/plastic properties must be overbent to compensate for the elastic part of the deformation. The overbend process, which is described in further detail below, can be defined as a closed loop control. Within the first bending step, the robot arm 606 moves to a new position. Preferably the new position is equal to the planned position or to the planned position plus an amount of overbending. At the end of the move the forces and moments acting on the grippers are measured. They indicate the remaining elastic deformation in the wire. To determine the gripper position which correspond to the released wire shape, the robot arm 606 starts a new move in direction opposite to the acting forces and moments. The forces correspond to a translational move, the moments to a rotational move. By adjusting continuously the movement direction to the measured forces and moments, the robot achieves a position, where the forces and moments are in the order of the measurement resolution (zero-force-position). By choosing an appropriate measurement resolution, the remaining elastic deformation can be neglected and the relative position of the two grippers corresponds to the relative position of the straight wire sections in the released situation. This zero-force-position is compared to the planned position. If the differences are bigger than the tolerance limits, an additional bending step follows to decrease the difference. From the zero-force-position the robot moves now in direction to the planned position and overrides the planned position about the value of the difference between zero-force and planned position. The endpoint of this move is called overbend position. From the overbend position starts again the force and moment controlled move to find the new zero-force-position. If the new zero-force-position is within tolerance limits to the planned position, then the bending process for one slot-to-slot bend is completed and the wire is fed to bend the next slot-to-slot section. If the amount of overbend was too much, the new overbend position is calculated as-described above. If the amount of overbend was not sufficient, then the new overbend position is calculated as the former overbend position plus the difference between new zero-force-position and planned position. The described process is repeated within a loop up to the situation, that the difference between zero-force-position and planned position is smaller than the tolerance limit.

Materials with shape memory properties and TMA will be bent to the planned position. To transfer this position into the memory of the alloy, the wire section between the two grippers is heated to a certain temperature for a certain time. The heating is possible e.g. by conductive resistance heating, laser, convection, radiation, or applying warm air or liquid to the material. Heating current and time must be appropriately adjusted to the respective alloy, the wire section length and the wire shape. To warm-up the wire, the wire heating can start already during the bending movement to the planned position. To avoid a heat sink effect at the gripper fingers and to ensure that the complete inter-bracket section of the wire obtains the necessary heating, the gripper fingers 652, 654 (FIG. 5) or at least the contact areas of gripper and wire are heated too. The grippers may be heated continuously during the production process of the whole archwire. To compensate for an incomplete transition of the bending position to the alloy memory, there can be defined a certain amount of overbending.

In bending TMA materials, the material can be heated to a high temperature where there is no springback, however when the material cools, it retains its springback properties. The procedure for bending such materials is as follows: 1) heat the gripper fingers; 2) bend the wire to the desired configuration; 3) heat the wire up to the temperature where the springback tendency no longer exists; 4) turn off the heat source and allow the wire to cool, and 5) advance the wire to the next position for bending; and then repeat steps 1)–5).

The bending of the wire from one section to the next requires that the location and alignment of one straight wire section (i), for example P3 to P4, is defined in reference to the previous straight wire section (i−1) in the counting order defined in the bending system. The origin of the bending system is defined at the end of the straight wire section (i−1), which aims towards the following straight section (i). The x-axis is equal to the direction of the straight wire section (i−1) directed to section (i). For wires with rectangular cross-section the y-axis is perpendicular to x and in direction to the wider dimension of the wire. For quadratic or circular cross-section the y-axis must be perpendicular to x and can be chosen according to practical reasons. The x,y,z-axis follow the right hand rule.

The bracket slot data as described above needs to be transformed to bending data for use by the robot controller 602. This is done by calculation, from the position of the bracket center point 834 (FIG. 14), to the position of the straight wire section center point (located along the middle of the wire, point 840 in FIG. 19).

Next, there needs to be a calculation of the bent wire shape and length. In FIG. 30, this is shown as the shape of the wire between points P2 and P3. For each bending step, the robot gripper grips the wire in a certain distance from the fixed gripper corresponding to the length of the wire between points P2 and P3. The wire section between the two grippers will be bent. To minimize the bending forces and moments and to ensure that the bending forces and moments don't exceed limits, which may cause damage to the equipment or to the wire, the gripped wire length should be approximately the "natural" length of the wire in its bent shape. If the length is too short, the wire will be torn and there will be high tensional forces, if it's too long, the wire will tend to kink.

The robot computer 600 therefore calculates the approximate shape of the bent wire using an appropriate algorithm. One way is deriving a second or third order curve representing the shape of the wire using numerical techniques. Another would be using a regular spline algorithm. Ideally, there should be no sharp bends in the wire. In the illustrated embodiment, a Bezier spline algorithm is used. The algorithm gives an analytical description of a smooth curve and generates a set of points along the length of the curve. The length of the curve is obtained by summing up the distance (in three dimensions) along each segment of the curve. The separation distance between each point in the segments can be set arbitrarily and in the illustrated embodiment is 0.05 mm. The algorithm is as follows:

Input:
  Centerpoint location and alignment of two neighbored straight wire sections (given as 4×4 matrice with local vector $\vec{1}$, tangential vector $\vec{t}$ normal vector $\vec{n}$ and vertical vector $\vec{v}$) These matrices correspond to the 4×4 matrix described earlier.
  tangential and antitangential distances $s_t$ and $s_{at}$
  Bezier-distance $b_d$ (empirical value)

Figure 20A:
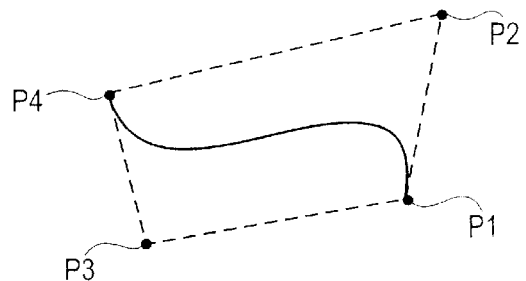
FIG. 20A is an illustration of four points and a curve defined by a Bezier spline, a technique used to calculate the shape of the bend in the wire between points P2 and P3 in FIG. 20.

The Bezier formula, as known by literature, is described by four points as shown in FIG. 20A.

The points of the spline curve are given by:

$$\vec{P} = (1-v)^3 \cdot \vec{P_1} + (1-v)^2 \cdot v \cdot \vec{P_2} + (1-v) \cdot v^2 \cdot \vec{P_3} + v^3 \cdot \vec{P_4} \, v \in \{0, \ldots, 1\}$$

Here it will be noted that the Bezier points $P_1$ to $P_4$ in FIG. 20A are not necessarily the points P1–P4 of the wire segments shown in FIG. 19, but rather are the points used to calculate the Bezier spline length and shape.

To describe the curved wire shape between the straight wire sections from slot (i−1) to slot i, the Bezier points $\vec{P_1}$, $\vec{P_2}$, $\vec{P_3}$, $\vec{P_4}$ are calculated by:

$$\vec{P_1} = \vec{l_{i-1}} + s_{t,i-1} \cdot \vec{t_{i-1}}$$

$$\vec{P_2} = \vec{l_{i-1}} + (s_{t,i-1} + b_d) \cdot \vec{t_{i-1}}$$

$$\vec{P_3} = \vec{l_i} - (s_{t,i} + b_d) \cdot \vec{t_i}$$

$$\vec{P_4} = \vec{l_i} - s_{at,i} \cdot \vec{t_i}$$

Figure 20B:
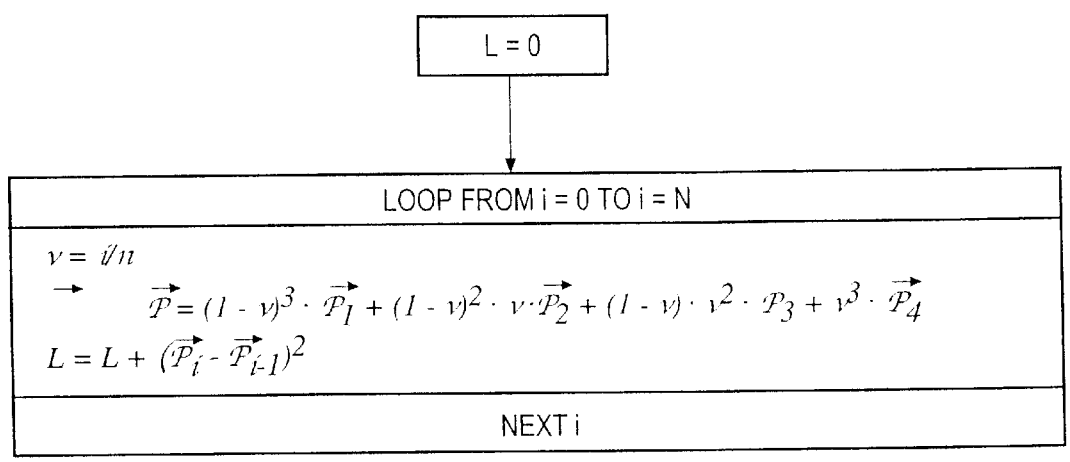
FIG. 20B is a flow chart of an algorithm to calculate the Bezier spline of FIG. 20A and the length of the curve.

The wire length L and the N intermediate spline points can be calculated by the algorithm shown in FIG. 20B.

The empirical value Bezier-distance $b_d$ must be set to make the calculated and actual bent wire shape tally. For orthodontic wires, a good assumption is $b_d$=1x . . . 2x the larger wire cross-section dimension.

The bending trajectory needs to be calculated for each bend. The bending trajectory is a number of positions of the moveable arm's gripper 651A in relation to the fixed gripper 651B, which connect the start position and the destination position of a bending movement. In general there are translational and rotational movement components from each bending trajectory position to the next.

Figure 29A:
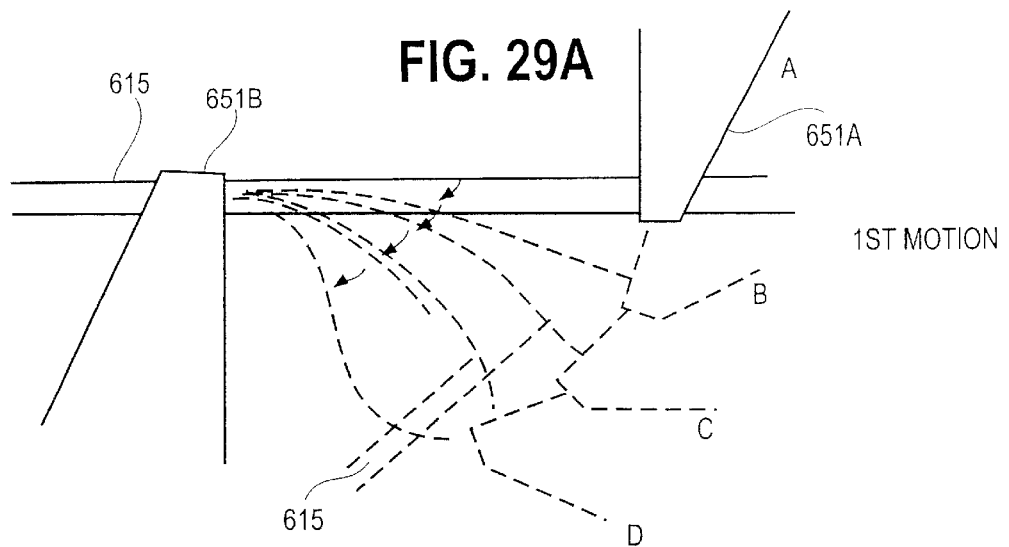
FIGS. 29A–29C illustrate how a bend may be formed in a series of steps.

For each bending trajectory position the calculated length of the curved wire must be equal to the calculated length in the planned position. To avoid kinking condition for the wire the movement can be divided into two parts:

1. Initial movement to steer the wire into a distinctly deformed shape. The initial movement is defined as a rotational transformation around an axis through the endpoint of the fixed gripper perpendicular to the connecting vector of the start position and the end position. This is indicated in FIG. 29A by the rotational motion of the moveable gripping tool 651B and movements a, b, c, and d.
2. Finish movement to destination position. The finish movement is a gradual approach from the start position (or if there is an initial movement from the end position of the initial movement) to the destination position. The translational and rotational parts of the whole bending movement are split up steadily to the individual bending trajectory positions. Between two bending trajectory positions, the movement path of the robot gripper is defined by a linear translational movement along the straight line connection of the two positions and by steadily divided rotational movement. The distance between two bending trajectory positions must be small enough to avoid kinking of the wire and inadmissible forces and moments. These movements are indicated at positions d, e, f, and g in FIG. 29B.

Figure 23:
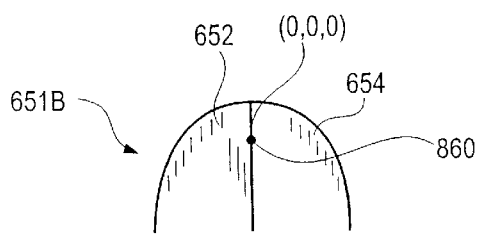
FIG. 23 is an elevational view of the gripping fingers of the fixed gripping tool of FIG. 6, showing the origin of a coordinate system used by the robot in bending wire.
Figure 24:
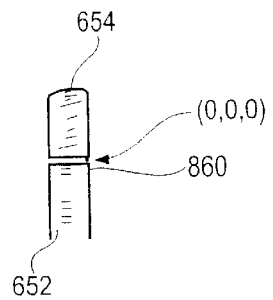
FIG. 24 is a top view of the gripping fingers of FIG. 23.

In bending wire as described herein, the robot system 604 of FIG. 2 has a coordinate system in which an origin 860 is defined as shown in FIGS. 23 and 24. The wire passes through the fixed gripping tool 651B through a small gap formed when the fingers are in an open position. The origin 860 is defined as the along the center of the axis of the wire at the planar edge of the fixed gripping tool 651B. The robot controller software knows the location of the moveable gripping tool relative to the fixed gripping tool in this coordinate system at all times. Furthermore, the wire is gripped by the moveable gripping tool at a precise point on the moveable gripping tool. Therefore, when the wire is held by the fixed gripping tool and the moveable gripping tool, the distance between the two is known exactly. This allows the bending shown in FIGS. 29A–29C to be executed without stretching or contracting the wire. In particular, the distance as measured along the wire between the fixed and moveable gripping tools at the point of attachment to the wire is constantly maintained a distance equal to the calculated Bezier distance for the wire as bent between the points P2 and P3 of FIGS. 19 and 20, and of course for subsequent bends.

To advance the wire between bends or to place the wire in condition for the first bend, there are at least two possibilities. One is that the moveable gripper tool grips the wire and pulls it through the fixed gripping tool (with the fixed gripping tool opened to allow the sliding of the wire with respect to the gripping tool). As an alternative, the wire could be on a spool or coil, and the spool rotated by a motor to advance the wire through the fixed gripping tool. In the later embodiment, a cutting tool will need to be provided to cut the wire after the bending is completed. Archwire manufacturers sell wires in bulk already cut to length and the present description is made in the embodiment in which the wire segment is advanced by the moveable gripping tool advancing the wire through the fixed gripping tool.

Having the bent wire between the two grippers in a tensed state, the robot gripper is moved to a new position, where no forces and moments are acting on the gripper. The force sensors 640 on the fixed and moveable gripping tools are used to determine the position. This position is called the zero force position and corresponds to the released state of the wire. Forces, moments and the movements components are calculated in the main robot coordinate system of FIGS. 23 and 24.

Depending on the nature of the material, some overbending of the wire may be needed. This would be indicated for example if the zero force position is not the same as the calculated position for the robot's moveable arm 606. To better understand the overbending principles, attention is directed to FIGS. 21 and 22

Figure 21:
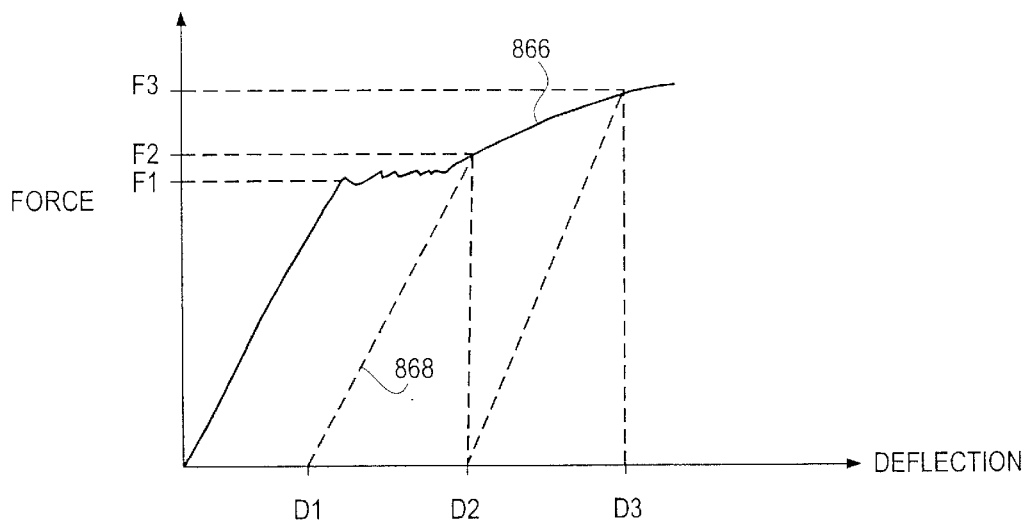
FIG. 21 is a graph of force as a function of deflection for a workpiece such as a wire. The graph illustrates that that when a certain amount of force, F1, is applied to the workpiece and then released, a deflection D2 results. When the force is released, the amount of remaining deflection, D1, is less than the deflection observed when the force is applied to the wire, D2, since the wire has elastic properties.

FIG. 21 illustrates the relationship between force and deflection of wire. The solid line 866 indicates how much force is needed to give a certain deflection of the wire. Where the force is less than F1, when the force is released the wire returns to its initial state and experiences no deflection due to elastic properties of the wire. At force level F1, some permanent deformation, i.e., plastic deformation, of the wire starts to take place. With a force level of F2, the wire is deflected an amount D2, but when the force is release from the wire the wire bends back to a deflection amount D1, with the relaxation curve 868 essentially parallel to the curve 866 up to force level F1, as shown. Thus, some level of force indicated at F3 is required to be applied to the wire such that when the force is removed the required deflection Ds is achieved in the wire. The fact that F3 is greater than F2 and that the deflection D3 is greater than D2 illustrates that some overbending is generally needed to yield the proper shape of the wire after the bending forces are removed.

Figure 22:
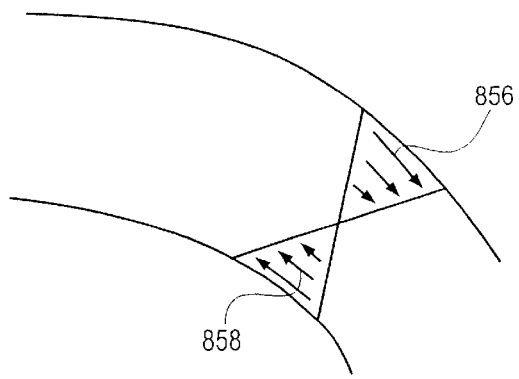
FIG. 22 is an illustration of the stresses found in a wire when it is bent.

FIG. 22 illustrates the stresses involved with wire material when it is bent. The wire has one portion experiencing elongation stress, as indicated at 856, while compression stresses are experienced at locations 858, with the length of the arrows indicating the relative magnitude of the stress. With small bends, the forces at the center of the wire are small enough such that only elastic deformation occurs, while at the outside portion of the wire some plastic deformation may occur. The result is that bending wire is a mixture of elastic and plastic deformation, the character of which is determined by the amount of the bend, the wire material, and the cross-sectional shape.

To determine the amount of required overbending, there are several possibilities. One is a purely analytical solution like finite element analysis of wire. Alternatively, a piece of wire can be tested to determine its response to known forces, and the result stored as a calibration table of bends. Basically, the curves in FIG. 21 are obtained experimentally. A more preferred approach uses force sensors 640 (FIG. 2A) on the fixed and moveable gripping tools to sense the zero force position of the wire and compare the location of the moveable gripper in this position with the intended position. A geometrical or deformation approach is another alternative. In this approach, the wire is bent some amount and then released, the relaxation position noted, the wire bent some more, the wire released, etc. the process continuing until the wire is bent to the desired position.

With a force based system, perhaps augmented by an adaptive, self-learning artificial intelligence type learning program or calibration table based on previous bends of similar wire, the resulting configuration of the wire can usually be achieved more quickly. Basically, for every bend performed in the wire, information is stored as to the movement necessary to result in a specific bend. For example, to achieve a 13 degree bend in the wire of type T and cross-sectional shape W, the wire had to be bent 15.5 degrees, and this information is stored. With enough data, a mathematical relationship can be derived that that represents curves 866 and 868 for the wire of type T (at least in the portion of the curve of interest), and this mathematical relationship can be used, in conjunction with force sensors, to quickly and accurately place the required bends in the wire.

In either situation, an optical system such as a camera could be used for detecting the position of the wire in the relaxed position is used to determine the actual shape of the wire after any given bend.

Figure 25:
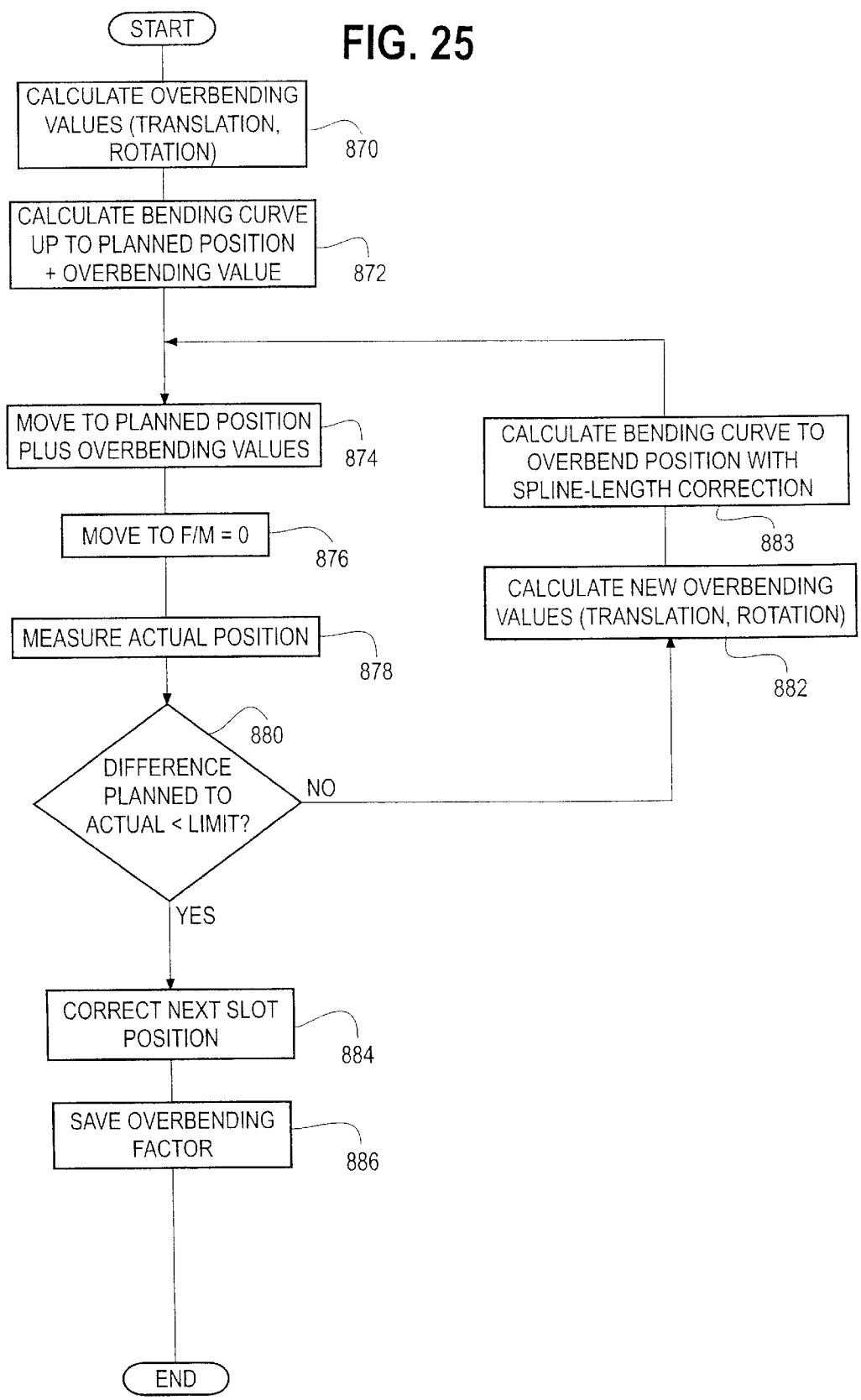
FIG. 25 is flowchart illustrating a deformation-controlled overbending procedure, which may be used to compensate for the elastic properties of the wire demonstrated by FIG. 21.

FIG. 25 is a flow chart of a deformation controlled overbending process that can be used with stainless steel or other wires, including shape memory wires where some overbending is still required.

At step 870, a calculation is made of overbending values in both a translation and rotational aspect. This calculation could be performed for example using finite elements methods, using a calibration table, using a derived mathematical relationship between force and bending, using stored values for overbending from previous bends, or some combination of the above.

At step 872, the bending curve is calculated up to the planned position and including the overbending values. This involves the Bezier spline algorithm set forth previously.

At step 874, the moveable gripping tool is moved to the position indicated by the sum of the planned position plus the overbending position. This forms a bend in the wire. Again, this position is determined in reference to the robot coordinate system and in reference to the spatial relationship between the points where a bend needs to be placed in the wire (P3 and P2 in FIG. 19, for example).

At step 876, the force sensors are used to measure the residual forces imparted by the wire onto the gripping tools, and if the forces are greater than some threshold, the moveable gripping tool 651A is moved to the position where the force measurement is zero or substantially zero.

At step 878 the actual position of the moveable gripping tool is measure using the position sensors in the moveable robot arm.

At step 880, a check is made to see if the difference between the actual position and the planned position is less than a limit. If not, new overbending values are calculated (step 882), and a new bending curve is calculated to overbend the wire an additional, amount, in the desired direction, to bring the wire closer to the desired shape (step 883).

Steps 874-883 are repeated until the difference between the actual position of the moveable gripping tool and the planned position is less than a limit.

At step 884, the error in the actual position relative to the planned position is noted and compensated for by correcting the next slot position. In particular, the next slot position represented by the next pair of points in the set of points in FIG. 19 is translated in three dimensions by the amount of the error. This correction of the next slot position is needed so as to avoid propagation of an error in any given bend to all subsequent bends.

At step 886, the overbending results from steps 874-882 are saved in memory and used in an adaptive technique for estimating future overbending requirements as explained above.

Figure 26:
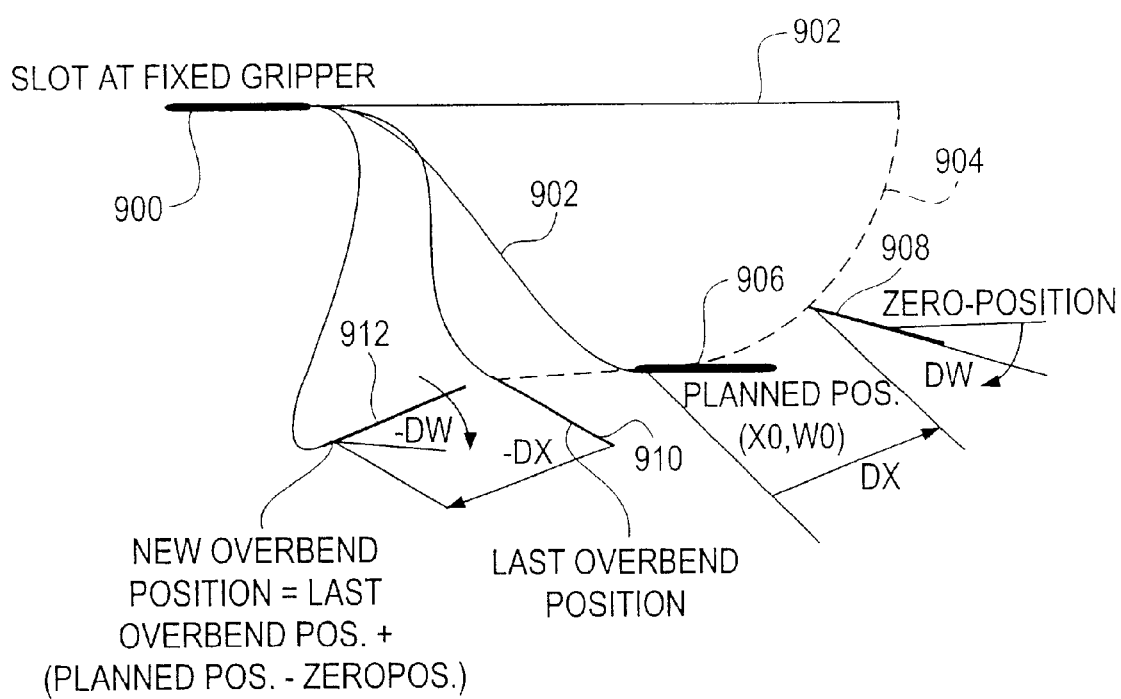
FIG. 26 is an illustration showing the overbending method set forth in FIG. 25.

FIG. 26 is a schematic representation of the overbending performed by the method of FIG. 25. The line 900 represents the slot between the fingers of the fixed gripper and the line 902 represents the wire in various stages of bending. The dashed line 904 indicates the movement of step 874, with line 906 representing the slot of the moveable gripping tool between the gripping fingers where the wire is gripped in the planned position. The zero force position where the moveable gripper is moved to is indicated at 908 (step 876 in FIG. 25). There is both a rotational (dw) and translational (dx) aspect to the difference between the zero force position and the planned position. The last overbend position is shown as position 910 (the overbend calculated at step 870). The required correction is shown by the position 912. This new overbend position, calculated at step 880 in FIG. 25, is equal to the last overbend position 910 plus the planned position 906 minus the zero position 908. This new overbend position includes both translational and rotational aspects as indicated by –dx and –dw.

Figure 27A:
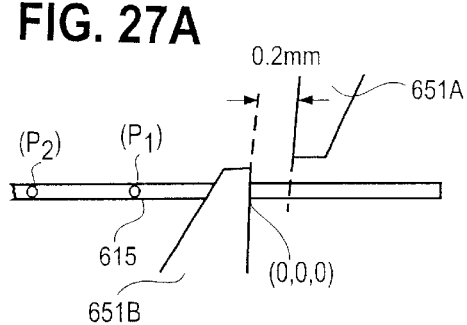
FIGS. 27A–27E are a series of schematic drawings of the fixed and moveable gripping tools of FIG. 6, showing how they moved relative to each other and grip and release the archwire to place the archwire in position to form a bend between points P2 and P3 of FIG. 19.
Figure 27B:
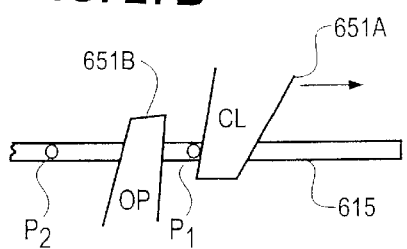
Figure 27C:
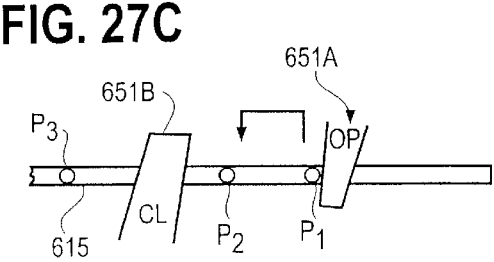
Figure 27D:
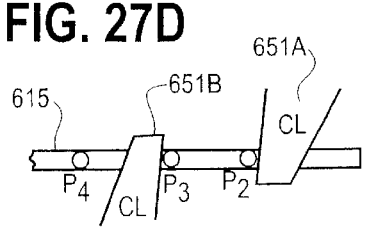

One possible example of actual robot gripper movements to feed the wire through the grippers and execute a representative bend will be explained conjunction with FIGS. 27A–28E. As shown in FIG. 27A, the wire is thread through the fixed gripper tool 651B or placed there by the moveable gripping tool such that some length of wire is extending beyond the end of the fixed gripping tool 651B. The points P1 and P2 along the wire segment are indicated. The moveable gripper tool 651A is positioned above and slightly to the right of the fixed gripping tool, here 0.2 mm away. The moveable gripping fingers open and the moveable gripper moves down to clamp the wire. The 0.2 mm distance is merely chosen so that the fingers to not collide and can vary from the illustrated embodiment. The fingers cooperate with each other by translation movements of the moveable gripping tool and releasing and closing the fixed and moveable grippers such that the wire is advanced through the fixed gripping tool. This is also indicated by FIG. 27B, showing the fixed gripping tool 651B open (OP) to allow the wire to be slid through a slot formed between the fingers of the tool 651B. The moveable gripping tool moves to the right to draw the wire through the fixed gripping tool until the point P2 is to the right of the fixed gripping tool (as shown in FIG. 27C), where it can be grasped by the moveable gripping tool. As shown in FIGS. 27C and 27D, the moveable gripping tool opens and releases its grip on the wire (indicated by OP) and moves to the position where it closes (CL) and grasps the wire at location P2. Then moveable gripping tool 651A draws the wire through the fixed gripping tool while gripping the wire at point P2, such that point P3 is located at the origin of the robot coordinate system, as shown in FIG. 27D. Since the planned location of both P2 and P3 after a bend in the wire is made is known in the robot coordinate system, the moveable gripping tool 651A moves to the position shown in FIG. 27B to place a bend in the wire. At this point, if further overbending is called for, the process of, e.g., FIGS. 25 and 26 is performed to place the required overbend in the wire. The movements of FIGS. 27B–27D could be combined to one movement if the distance is small enough, and depending on the thickness of the wire.

Figure 27E:
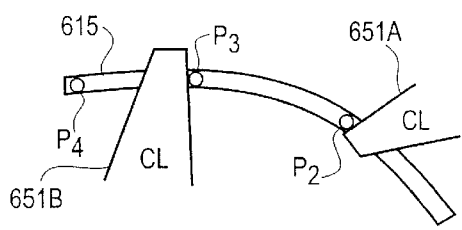
Figure 28:
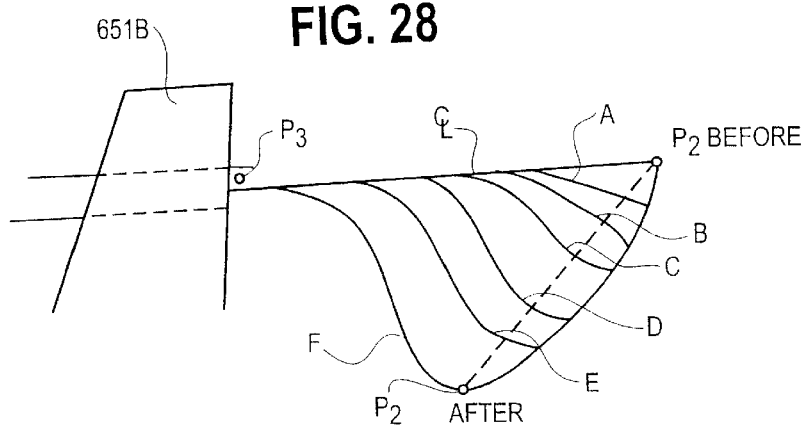
FIG. 28 is a schematic illustration showing how the movable gripping tool bends an archwire while maintaining a constant distance from the fixed gripping tool.
Figure 29B:
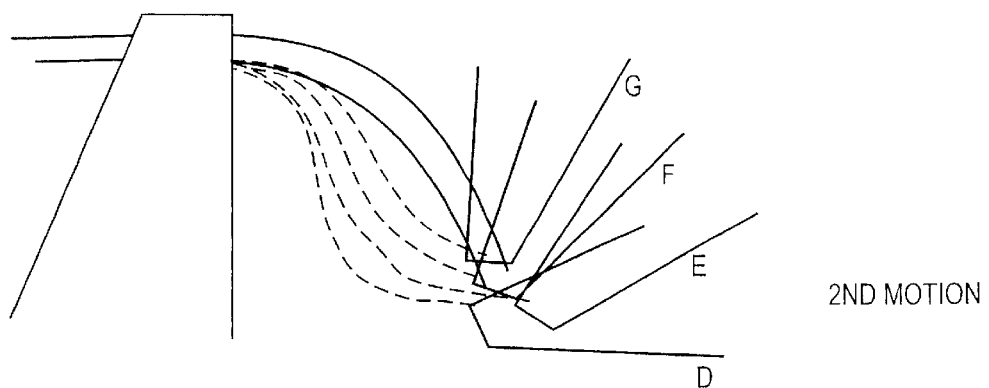
Figure 29C:
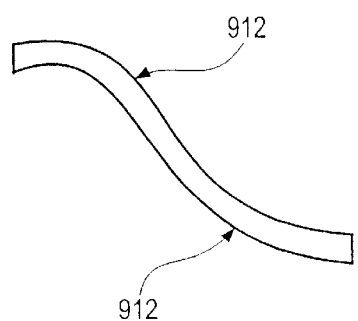

FIG. 28 illustrates before and after positions of the wire when the bending of FIG. 27E occurs. The figure illustrates that the movement of FIG. 27E is not a straight line movement which might cause excessive elongation or kinking of the wire. Rather, the movement of the gripper is illustrated as steps a, b, c, d, e, f such that the distance, as measured along the length of the wire, is maintained constant. The movement may performed in two stages (such as shown in FIGS. 29A and 29B). The result is that two bends 912 are placed in the wire, as shown in FIG. 29C. Of course, a twist could also be performed in the wire if required by the prescription.

Figure 30A:
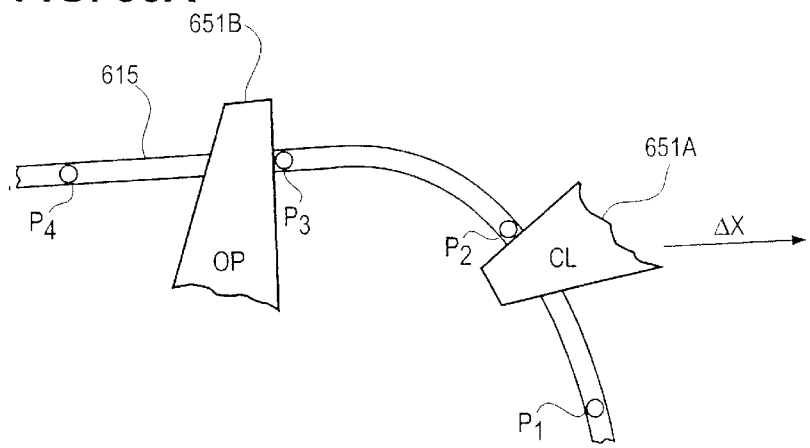
FIGS. 30A–30D are a series of schematic drawings of the fixed and moveable gripping tools of FIG. 6, showing how they move relative to each other to place the archwire in position to form a bend between points P4 and P5.
Figure 30B:
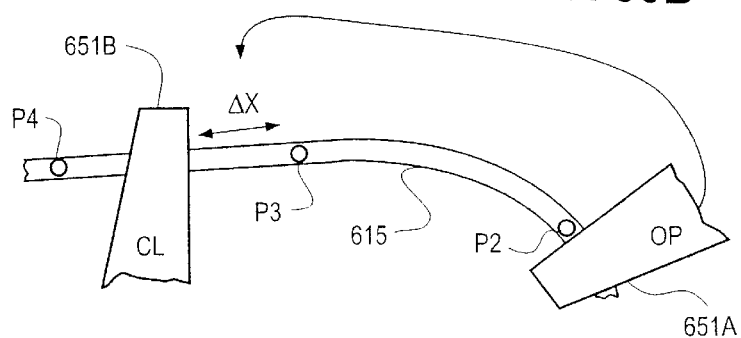
Figure 30C:
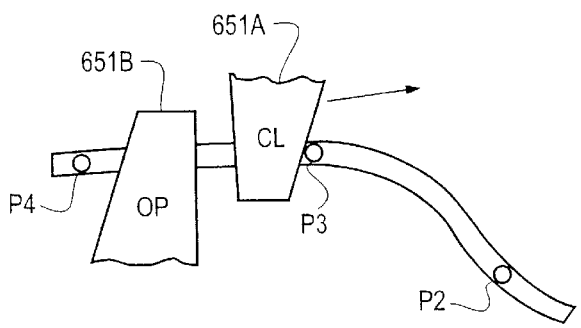
Figure 30D:
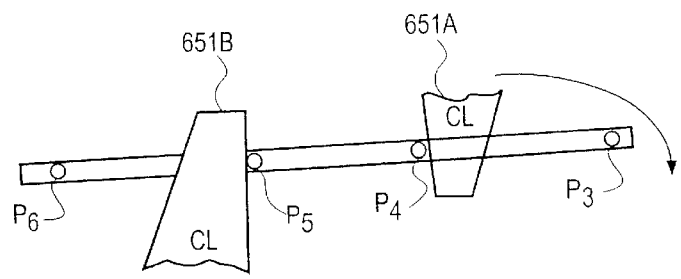

After the bend has been placed in the wire, the steps shown in FIGS. 30A–30D are performed to advance the wire along to the position of the next bend. First, as indicated at FIG. 30A, the moveable gripping tool 651A is translated to the right an amount indicated by $\Delta X$. This moves point P3 to the right of the fixed gripping tool by an amount $\Delta X$, as shown in FIG. 30B. Then, the moveable gripping tool releases the wire and re-grips the wire to the right of the fixed gripping tool as shown in FIG. 30C and again translates to the right an amount sufficient to move point P4 to the right of the fixed gripping tool. The moveable gripping tool releases the wire again and grips the wire at point P4. The wire is again translated to the right such that the situation shown in FIG. 30D is obtained. The wire is now in position for a bend in the wire between P4 and P5. The process of FIGS. 25 and 26 occurs again to calculate new bending and overbending positions and the bend is formed in the wire. The process of FIGS. 30A–30D continues until all the bends have been formed in the archwire. When the final bend is complete, the wire is released from the moveable gripper at the exit location of the wire manufacturing system, and carried by conveyor to the labeling and packaging station described earlier.

Shape memory alloy materials require heating to take on the shape given by the bend produced in FIG. 27E. Thus, for these wires, while the wire is held in the position shown by FIG. 27E, heat is applied to the wire to raise the temperature of wire to the value needed to take the set. The temperature varies with the type of material. In the illustrated embodiment, a resistance heating system is used as described previously. The current is adjusted until the proper temperature is reached. The heat treating is deemed complete when the force sensors read zero (or less than some limit) when the wire is held by the grippers in the planned position. The amount of current and time applied to the wire is again stored information that can be used for future heating of the same type of wire.

For some softer shape memory materials, e.g., NiTi, the force sensor 640 (FIG. 2A) provided in the gripping tools must be very sensitive to detect the small forces involved. While shape memory materials may not require force sensors at all, they can be used to give information as to the effectiveness of the heating process.

In a preferred embodiment, two force sensors are used. A coarser force sensor, used for measuring larger forces during bending, is fitted to the moveable gripping tool. A finer force sensor, with a higher resolution, low noise and higher sensitivity, e.g., with a sensitivity of less than 0.0005N, is fitted to the fixed gripping tool, in order to detect the zero force position. The force sensors are both based on strain gauge technology and can be readily adapted from commercially available strain gauges or off the shelf units. For example, the finer force sensor may have different amplifiers or other modifications to the circuitry to have greater sensitivity, signal to noise ratio and force resolution. Other types of force sensors, such as those based on piezo technology, would be suitable. Suitable off-the-shelf strain gauge force sensors are available from JR3 Inc. of Woodland Calif., model nos. 45E15A-U760 (fixed gripping tool) and 67M25A-I40(moveable gripping tool).

Other types of heating systems could be adopted for archwires and other types of workpieces to be bent, such as laser, flame, infrared, conductive or radiant heating. Some springback may still be observed in shape memory materials even when heating is performed unless the wire is heated close to the maximum permitted temperature of the wire. Therefore, with some shape memory materials it may be desirable to perform some overbending in order to lower the temperature needed to set the new shape into the wire. Again, the required amount of overbending at a given wire temperature can be stored in memory and used to derive a relationship between temperature, overbending and resulting position for the material, which can be used for subsequent bends in the wire.

Due to the complexities of wire deformation and twisting in wire that can occur when wire of a rectangular cross section is bent, and the difficulty in controlling the resulting shape of the wire (particularly when complex bends and twists are formed in the wire), the usage of force measuring devices, and position sensors to detect the shape of the wire when the wire is in a zero force condition, gives accurate information as to the shape of the wire after a bend. Thus, a force based approach to overbending is a preferred embodiment. The actual position of the wire in the zero force condition can be obtained by position sensors on the robot arm (which makes no contribution to the measurement of forces), or better yet, by releasing the wire from the moveable arm and detecting the position of the wire with a camera or other optical system. Basically, the camera would image the wire immediately in front of the fixed gripping tool. Pattern recognition and image processing algorithms are used to determine the edge of the wire, and thereby calculate its shape. More than one camera could be used if necessary to image the wire sufficiently to calculate twist in the wire. The effects of gravity would have to be compensated for in any position measuring system in which the wire is not held by the moveable gripping tool.

Thus, in one possible embodiment the robot further comprises an optical sensor system such as a CCD camera detecting the shape of the orthodontic appliance after the bend in said orthodontic appliance has been made, such as by releasing the appliance from the moveable gripping tool and allowing the appliance to take its natural position, and then using the optical system to detect the shape of the appliance.

It is also possible to use both the force measuring systems and the optical system as a final check on the shape. The force sensor system (e.g., coupled to the fixed and/or moveable gripping tools) detects forces generated by the orthodontic appliance after the orthodontic appliance has been bent. The moveable arm is operated to move the orthodontic appliance to a zero-force position in which the forces detected by the force system are below a predetermined threshold. The optical sensor system detects the shape of the orthodontic appliance in the zero-force position. The position detected by the optical sensor system can be used as a feedback mechanism for further wire bending if the zero force position is not the intended or desired configuration of the appliance. An optional type of sensor system would be calipers that contact the workpiece and responsively provide position information as to the location (i.e., bend) formed in the workpiece.

Figure 31:
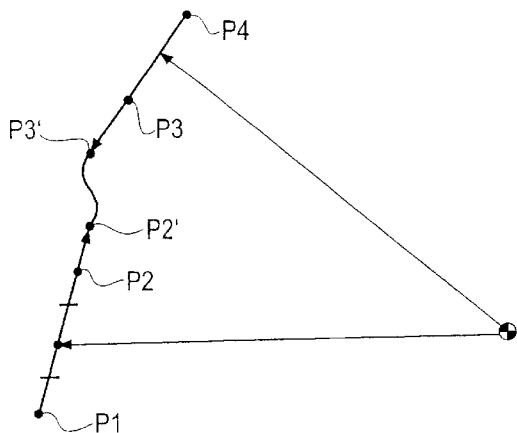
FIG. 31 is an illustration of the points defining a portion of an archwire, and illustrating a technique for placing bends in wires where a substantial distance exists between the straight wire segments.

For stainless steel wires, there is generally no need for heat treatment of the wire. It is simply bent into the desired position, with overbending performed as required. The shorter the distance between endpoints of a bend, the greater the deformation in the wire, therefore the greater the predictability in the deformation. With orthodontic archwires, the situation can occur where there is a relatively long distance between bracket slots (particularly in the region of the molars) and it can be difficult to obtain a stable bending result. A preferred solution here is to make this distance shorter by adding on some length to the tangential distance of one slot position and the antitangential distance of the next slot position, as shown in FIG. 31. Here, point P2 is extended in space to point P2', and point P3 is brought closer to point P2 by moving it to point P3'. The required bending of the wire is now calculated relative to points P3' and P2'. The bend placed between P3' and P2' is now sufficiently short that it can be formed with enough control.

Figure 32:
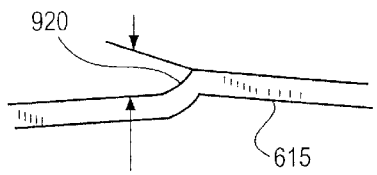
FIG. 32 is an illustration of a portion of an archwire showing a bend formed therein to increase the forces applied by the wire when the wire has nearly straightened out, e.g., near the end of treatment.
Figure 33:
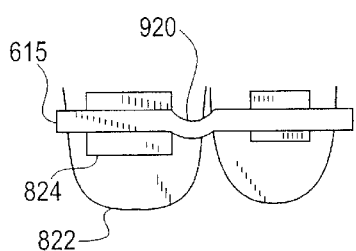
FIG. 33 shows the wire segment of FIG. 32 installed between two teeth.

In practice, it known that after an archwire has been fitted to the patient's brackets, the archwire imparts forces to move the teeth to the desired position. However, after a certain amount of time, some small amount of bend remains in the wire but it is insufficient to cause any further tooth movement. Consequently, the teeth are not moved to their desired position. This can be compensated for by adding an additional amount of bend to the wire so that when the wire is installed, it will continue to exert forces until the teeth have been moved all the way to their desired position. As shown in FIG. 32, this small additional bend is shown as 920. FIG. 33 shows the wire of FIG. 32 installed in the brackets of a patient. The bend 920 of FIG. 32 is in addition to other bends that may be placed between the brackets 824. FIG. 33 illustrates that enough residual force exists by virtue of bend 920 to move the teeth 822 to their desired position.

Figure 34:
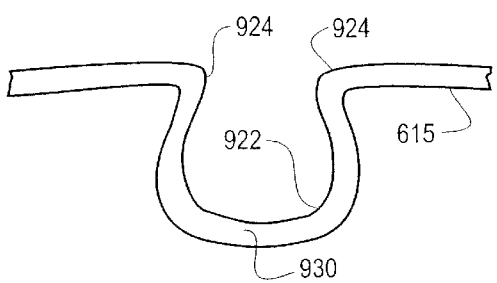
FIGS. 34 shows a wire with a loop in the wire.
Figure 35A:
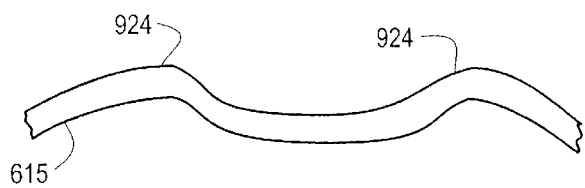
FIGS. 35A–35B illustrate one possible method of forming the loop in the wire of FIG. 34.
Figure 35B:
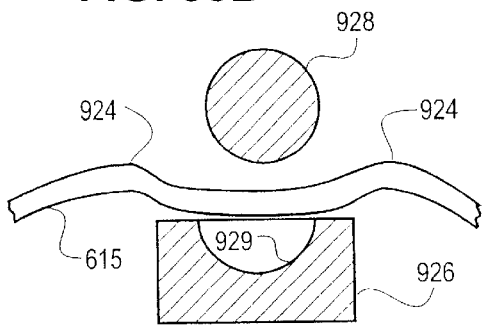

In certain orthodontic situations, loops may need to be bent in the wires. FIG. 34 illustrates a loop 922 formed in a wire 615. The loop may be formed by the robot of FIG. 34. Alternatively, only the peripheral corners 924 of the loop 920 are formed by the bending robot, as shown in FIG. 35A, with the remainder of the loop formed by placing the wire over a die 926 having a shape 928 matching the shape of the bottom portion 930 of the loop 920. A forming tool 928 is moved against the wire and die 926 to form the bottom portion of the loop as indicated in FIG. 35B.

The robot may also include a separate arm or tooling by which stops, or other features are bonded to the wire by suitable techniques such as welding. For example, the robot can be fitted with other tools for forming a Herbst appliance or expansion devices. Alternatively, different types of wires could be joined together by welding.

The robot may also be used to bend clear, transparent wires made from polymeric or plastic materials, such as thermoplastics, duroplastics, polyacrylic plastics, epoxy plastics, thermoplastics, fiber reinforced composites, glass fiber containing materials or other similar materials suitable for an orthodontic archwire. These plastics archwires may require heating during bending, but current sources may not be suitable heating devices. Recommended techniques for heating the plastic wire include blowing hot air over the wires during bending, using heated pliers, placing a heat conductive material onto the wire, using a laser to heat the wire, or spraying a hot vapor or liquid onto the wire.

As noted above, additional possibilities are presented for bending fixation plates, orthotic devices, prosthetic devices, endodontic devices, surgical guidewires, surgical archbars, implants or surgical tools with the robot manufacturing system. The gripper fingers and associated structures may be optimized depending on the workpiece or appliance in question. However, the principles of operation are basically the same.

For example, the robot of the present invention is particularly useful for bending fixation plates, rods, compression plates and the like, for example facial, cranial, spinal, hand, and long bone and other osteosynthesis plates, such as, for example, the titanium appliances provided by Leibinger Gmbh of Germany. These fixation plates may consists of, for example, an elongate skeletal frame having a plurality of apertures for receiving screws, arranged in straight lengths, C, Y, J H, T or other shape configurations, or a long cylindrical rod. At the present, these appliances are manually bent by the surgeon to the shape of the bone in the operating room using special manual bending tools. It is possible to automate this process and bend the plates in advance using the principles of the present invention. In particular, the shape of the bone or bone fragments is obtained a CAT scan, from a scan of the exposed bone using a hand-held scanner (such as described in the patent application filed concurrently of Rudger Rubber et al. SCANNING SYSTEM AND CALIBRATION METHOD FOR CAPTURING PRECISE THREE-DIMENSIONAL INFORMATION OF OBJECTS, Ser. No. 09/834,593, the contents of which are incorporated by reference herein. Once a three-dimensional virtual model of the bone is obtained, e.g., from CAT scan data, the virtual model is manipulated using a computer to fuse the bones together in the desired position. The surgeon then overlays the three-dimensional virtual implant in the desired location on the virtual model, and bends the virtual implant using the user interface of a general purpose computer storing the virtual model of the bone and implant. The required shape of the implant to fit the bone in the desired location is derived.

Alternatively, a physical model of the bone in the desired configuration can be manufactured from the virtual model using stereolithography (SLA), three-dimensional lithography, or other known technology, and the shape of the implant derived from the physical model.

As another alternative, a SLA physical model of the bones (e.g., skull) is made from a CT scan or other source, and the surgeon performs a simulated surgery on the physical model to place the bones in the desired condition. The model is then scanned with an optical scanner and a virtual model of the bones in the desired condition is obtained, as described in the patent application of Rudger Rubbert et al., cited above. The virtual fixation device is then compared or fitted to the virtual model of the bones to arrive at a desired shape of the fixation device.

In either situation, the shape of the implant is then translated to the robot controller as a series of straight sections and bends of known geometry (and specifically position commands for the moveable gripping tool relative to the fixed gripping tool). The moveable and fixed gripping tools of the bending device grip the implant or fixation device at one end and then either bend the appliance or advance the position of the implant to the location of the next bend, and continue along the length of the device to form the device in the desired configuration. Obviously, some modification to the gripping tools may be needed from the disclosed embodiment depending on the physical characteristics of the device being bent, and such modifications are within the ability of persons skilled in the art.

The bending apparatus described above is also adaptable to generic workpieces, such as tubes, cylinders, wires or other types of structures.

The bending apparatus may use resistive heating, force sensors, overbending, and the other features described at length in the context of orthodontic archwires, depending on the application for other workpieces.

While presently preferred embodiments of the invention have been described for purposes of illustration of the best mode contemplated by the inventors for practicing the invention, wide variation from the details described herein is foreseen without departure from the spirit and scope of the invention. This true spirit and scope is to be determined by reference to the appended claims. The term "bend", as used in the claims, is interpreted to mean either a simple translation movement of the workpiece in one direction or a twist (rotation) of the workpiece, unless the context clearly indicates otherwise.

What is claimed is:

1. A gripping tool for a bending apparatus, said bending apparatus comprising a robotic arm moveable about multiple axes, comprising:

a pair of opposing gripping fingers moveable between open and closed positions, said pair of opposed gripping fingers mounted to the end of said robotic arm, said gripping fingers for gripping a workpiece and thereby bending and/or twisting said workpiece by virtue of movement of said robotic arm while gripping said workpiece while a first portion of said workpiece remains fixed relative to said gripping fingers;

a force system coupled to said gripping fingers for detecting forces imparted by a workpiece either during bending or after a bend has been placed in said workpiece; and a heating system for heating said opposing gripping fingers above ambient temperature.

2. The gripping tool of claim 1, further comprising a resistive heating System supplying a current to said gripping tool so as to apply resistive heat to said workpiece.

3. A gripping tool for a bending apparatus for bending orthodontic archwires, said bending apparatus comprising a robotic arm moveable about multiple axes and a fixed gripping tool, comprising:

a pair of opposing gripping fingers moveable between open and closed positions, said pair of opposed gripping fingers mounted to the end of said robotic arm, said gripping fingers for gripping an orthodontic archwire and thereby bending and/or twisting said orthodontic archwire by virtue of movement of said robotic arm while gripping said orthodontic archwire arid while a first portion of said workpiece remains held by said fixed gripping tool; and wherein said pair of opposed gripping fingers and fixed gripping tool are operative to advance said orthodontic archwire through said fixed gripping tool in a series of steps and bend successive segments of said orthodontic archwire to thereby form a completed orthodontic archwire having a predetermined shape.

* * * * *